(12) United States Patent
Eibl

(10) Patent No.: US 6,344,576 B1
(45) Date of Patent: Feb. 5, 2002

(54) PHOSPHOLIPID-ANALOGOUS COMPOUNDS

(75) Inventor: Hans-Jörg Eibl, Bovenden (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 09/486,039

(22) PCT Filed: Aug. 18, 1998

(86) PCT No.: PCT/EP98/05252

§ 371 Date: May 17, 2000

§ 102(e) Date: May 17, 2000

(87) PCT Pub. No.: WO99/09037

PCT Pub. Date: Feb. 25, 1999

(30) Foreign Application Priority Data

Aug. 18, 1997 (DE) .......................... 197 35 776

(51) Int. Cl.⁷ .............................. C07F 9/02; A61K 9/27
(52) U.S. Cl. ............................ 554/82; 554/79; 554/80; 424/450
(58) Field of Search .............................. 554/82, 79, 80; 424/450

(56) References Cited

FOREIGN PATENT DOCUMENTS

| DE | 240020 A1 | * 8/1985 | |
| DE | 240 020 | 10/1986 | ............. C07F/9/10 |
| EP | 0002202 A2 | * 11/1978 | ............. C07F/9/09 |
| EP | 0 002 202 | 6/1979 | ............. C07F/9/09 |
| WO | 97 30058 | 8/1997 | ............. C07F/9/10 |

OTHER PUBLICATIONS

XP 000672277, Maruyama et al, Phosphatidyl polyglycerols prolong liposome circulation in vivo. Apr. 11, 1994, International journal of pharmeutics 111(1994) 103–107.*

Maruyama et al., "Phosphatidyl Polylycerols Prolong Liposome Circulation in Vivo", International Journal of Pharmacognosy, vol. 111, 1994, pp. 103–107.

* cited by examiner

Primary Examiner—Sreeni Padmanabhan
Assistant Examiner—Diedra Faulkner
(74) Attorney, Agent, or Firm—Fulbright & Jaworski, LLP

(57) ABSTRACT

The present invention relates to phospho-lipid compounds of formula

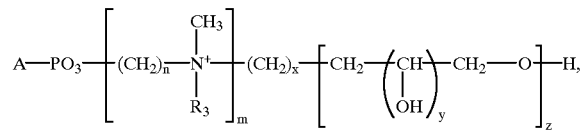

having solubilizing activity for water-insoluble or poorly water soluble active agents and their use in the delivery of active agents to cells and in the treatment of diseases, i.e., cancer and protozoal diseases. The compounds also exhibit direct therapeutic effects on some diseases. The inventive compounds can be formulated into liposomes containing phospholipids, alkylphospholipids and/or cholesterol. The compounds of the present invention may be prepared by reacting primary and secondary amines with epoxides.

31 Claims, No Drawings

PHOSPHOLIPID-ANALOGOUS COMPOUNDS

This is the U.S. National Stage Application of PCT/EP98/05262 filed Aug. 18, 1998.

DESCRIPTION

The invention relates to novel phospholipid-analogous compounds which can be employed as liposome constituents for transporting pharmaceuticals, as solubilizers for pharmaceuticals of low solubility in water and also as active ingredients themselves for disorders such as cancer and leishmaniosis, to liposomes containing these novel compounds, to pharmaceutical compositions which contain these liposomes, and to processes for producing pharmaceuticals.

The invention relates in particular to phosphatidyl compounds which contain a defined hydrophilic radical, and to liposomes which have a shortened or lengthened lifespan in the serum and can be taken up specifically by particular cells, for example tumour cells.

The retention time of conventional liposomes in the serum is up to 5 hours. However, it is desirable, especially when liposomes are used as carriers of active pharmaceutical ingredients, for the liposome retention time in the blood circulation to be as long as possible, but especially in conjunction with uptake in selected target cells.

Hence the so-called stealth liposomes which have a lengthened lifespan were developed. These stealth liposomes have a structure based on phosphatidyl compounds which contain an extended polyethylene glycol residue. The polyethylene glycol residue proved to be most effective for the desired lengthened lifespan with molecular weights between 2000 and 3000. A considerable disadvantage of these stealth liposomes and of the phosphatidyl compounds with polyethylene glycol residue is, however, that they are not accurately defined compounds because the polyethylene glycol residues have different chain lengths. However, the so-called stealth liposomes always have, as a consequence of the phosphate radical, a negative surface charge in the liposome membrane. The object of our own earlier patent application 196 22 224.9 was therefore to provide compounds which increase the lifespan of liposomes and have a composition which can be stated accurately, likewise using phosphate esters and thus negative charges.

An object of the present invention is, by contrast, to provide compounds which avoid this negative surface charge and link the oligoglycerol or sugar residues by a nitrogen atom into the structure. The positive charge on the nitrogen residue balances the negative charge on the phosphate, or even overcompensates when 2 nitrogen atoms are used in the molecule. This object is achieved according to the invention by a compound of a general formula I $$A-PO_3^- \left[ -(CH_2)_n - \overset{CH_3}{\underset{R_3}{N^+}} - \right]_m \left[ -(CH_2)_x - \left[ CH_2 - \left( \underset{OH}{CH} \right)_y - CH_2 - O \right]_z - H \right]$$

in which A a is $CH_2-O-R_1$ or $CH_2-O-R_1$
   $CH-O-R_2$      $CH-O-$
   $CH_2-O-$       $CH_2-O-R_2$ b is $CH_2-O-R_1$ or $CH_2-O-R_1$ or $CH_2-O-$
   $(CH_2)_s$      $CH-O-$       $CH-O-R_1$
   $CH_2-O-$       $(CH_2)_s-H$  $(CH_2)_s-H$ where $R_1$ and $R_2$ are, independently of one another, hydrogen, a saturated or unsaturated acyl or alkyl radical which can optionally be branched or/and substituted, where the total of the carbon atoms in the acyl and alkyl is 16 to 44 C atoms, s is an integer from 0 to 8, c is a radical of a primary or secondary alcohol of the formula RO—, where R is a saturated or unsaturated alkyl radical, mainly with cis double bond, of from 12 to 30 carbon atoms, n is an integer from 2 to 8, $R_3$ a can be 1,2-dihydroxypropyl or b can be alkyl with 1 to 3 C atoms when z is >0 or c can be alkyl with 1 to 3 carbon atoms when n≠2 and z=0, m is 1 or 2, x is an integer from 0 to 8, y is 1 for z=1 to 5 or is 1 to 4 for z=1 z is an integer from 0 to 5.

Preferred compounds are those where $A= CH_2-O-R_1,$
    $CH-O-R_2$
    $CH_2-O-$ m=1, n=2, x=0, z≠0, and $R_3$ is an alkyl radical, do not apply simultaneously.

The structural elements used in the substances described herein can be varied at will and adapted to suit the particular use.

It is possible via structural parameter A to vary mainly the apolar portions of the molecules, for example via the chain length of the fatty acids and of the alkyl radicals. A modification of the polar portions is possible via the phosphate group, the nitrogen atom and the oligoglycerols linked thereto.

The compounds embraced by the general formula I have excellent biological properties and are used as 1) liposome constituents for specific accumulation of active ingredients in target cells,
2) solubilizers for substances which are difficult to administer intravenously such as, for example, Taxol,
3) active ingredients for cancer and protozoal diseases.

The compounds which have particular importance for the various applications are now described in detail. There are overlaps in this because disubstituted glycerols with the structural feature A may have both membrane-stabilizing properties ($R_1+R_2>20$ C atoms) and membrane-destabilizing properties ($R_1+R_2<20$ C atoms). In particular, the boundary regions between membrane- and micelle-formers may be of special interest here.

It is common to all the structures that the novel molecules are simple to prepare, this being possible by reacting primary or secondary amines with epoxides. Thus, 1,2-dipalmitoyl-sn-glycero-3-phospho(N-methyl)ethanolamine with benzylglycidol results, after catalytic debenzylation and methylation on nitrogen, in a phospholipid with a lecithin-like structure which is used as liposome constituent.

Compounds with only one long alkyl or acyl chain have other interesting properties if they are linked via primary or secondary amines to epoxides, as is evident from the description hereinafter. They are excellent solubilizers for active ingredients which are difficult to administer intravenously and are in fact direct active ingredients for cancer and leishmaniasis.

The stepwise assembly, on which this invention is based, of the hydrophilic radicals of the phosphatidyl compounds of the formula I makes it possible to take an accurately defined composition of the compounds.

Thus the compound of the formula I according to the invention does not comprise a mixture of different molecules of indefinite composition and chain length; on the contrary, it is possible to obtain specifically a desired structure. This means that, if the desired product is an N,N-dimethyl-N-(2-hydroxypropyl-3,1-O,O-dihydroxypropyl)ammonium derivative with $y=1$ and $z=2$ in formula I, the compound is chemically defined and contains no portions with $y=1$ and $z=1$ or $y=1$ and $z=3$ etc. Hydroxypropyl derivatives having a wholly defined chain length and essentially free of other chain lengths are preferably used.

The compound of the formula I is, according to the invention, a homogeneous compound of defined structure. The compound is preferably more than 99% homogeneous in relation to the value of z. However, it is also possible to provide the compound with a homogeneity of more than 99.9% in relation to the value of z.

The compound preferably comprises hydroxypropyl derivatives on the nitrogen with 1 to 5 hydroxypropyl units, preferably with 1 to 3 hydroxypropyl units. Preferred in this connection are 1,3-linked linear oligoglycerol residues which are linked via a 2-hydroxypropyl radical to the nitrogen atom.

The radical for $A=c$ with the formula RO— is derived from the primary or secondary alcohol. When RO— is derived from a secondary alcohol, radicals with the oxygen on the $C_2$, $C_3$ or $C_4$ atom are preferred.

The radicals $R^1$ and $R^2$ are according to the invention preferably independently of one another hydrogen, a saturated or unsaturated acyl or alkyl racial which may optionally be branched or/and substituted, where the total of the carbon atoms in the acyl and alkyl is between 16 and 44.

The invention further relates to liposomes which contain phospholipids or/and alkylphospholipids, where appropriate cholesterol and 1 to 50 mol % of a compound of the general formula I.

The phospholipids or/and alkylphospholipids can be, for example, diacylglycerophospho compounds of defined structure. It is generally possible to employ these constituents of the lipids as compounds of defined structure.

In the case where $y>1$, the radical —$CH_2(CHOH)_y$—$CH_2$—OH is preferably derived from sugar alcohols which have 3 hydroxyl groups for $y=2$, 4 hydroxyl groups for $y=3$ and 5 hydroxyl groups for $y=4$. Examples of such radicals are mannitol derivatives for $y=4$, lyxitol derivatives for $y=3$ and threitol derivatives for $y=2$.

The liposomes according to the invention have a distinctly modified half-life in the blood circulation. The liposomes with $m=1$ are neutral to the outside and show increased retention times in the blood, while the liposomes with $m=2$ circulate for only a very short time as a consequence of the excess positive charge in the membrane.

The invention further relates to a pharmaceutical composition which contains the liposomes described above and one or more active pharmaceutical ingredients entrapped in the liposomes, where appropriate together with pharmaceutically customary diluents, excipients, carriers and bulking agents.

It is possible as a rule to use as active ingredients all active ingredients which can in fact be introduced into the plasma by means of liposomes. Preferred groups of active ingredients are, on the one hand, cytostatics, in particular anthracycline antibiotics such as, for example, doxorubicin, epirubicin or daunomycin, with doxorubicin being particularly preferred. Further preferred cytostatics are idarubicin, hexadecylphosphocholine, 1-octadecyl-2-methyl-rac-glycero-3-phosphocholine, 5-fluorouracil, cis-platinum complexes such as carboplatin and Novantrone, and mitomycins.

Further preferred groups of active ingredients are immunomodulating substances such as, for example cytokines, with particular preference being given among these in turn to the interferons and, in particular, α-interferon, substances with antimycotic activity (for example amphotericin B) and active ingredients for protozoal diseases (malaria, tyrpanosomal and leishmania infections). Taxol is likewise preferred as active ingredient.

Another preferred group of active ingredients are lytic active ingredients like those described in DE 41 32 345 A1. Preference is given to miltefosin, edelfosin, ilmofosin and SR162-834. Particular preference is given to alkyphosphocholines also with extended alkyl chains, for example erucylphosphocholine and erucylphosphocholines with increased phosphonitrogen distance.

The present invention further relates to the use of liposomes according to the invention for producing an antitumour composition, in which case the active ingredient is particularly preferably doxorubicin.

The present invention furthermore relates to the use of the liposomes according to the invention for producing a composition for influencing cell proliferation, in which case the active ingredient is a cytokine, particularly preferably α-interferon.

The liposomes according to the invention are prepared by methods known per se using apparatus customary for this purpose. It is possible typically to convert a solution containing the various components of the liposome, including 1 to 50 mol % of a compound of the formula I, into a lipid suspension which is then forced under high pressure through nozzles or through perforated plates, it being possible to control the size of the resulting liposomes by the size of the orifices in the perforated plate. Suitable measures for converting a lipid suspension into liposomes are known to the skilled person. Preferably, 5 to 55 mol % of a compound of the general formula I are converted with 35 to 60 mol % of cholesterol and 40 to 60 mol % of phospholipids or/and alkylphospholipids into a lipid suspension which is then converted by suitable measures in a manner known per se into liposomes. Such known processes can also be used to produce a pharmaceutical preparation which contains the liposomes according to the invention and one or more active pharmaceutical ingredients. For entrapping water-insoluble active ingredients, the active ingredient is dissolved together with the lipid constituents while, for entrapping water-soluble active ingredients, an aqueous solution containing the water-soluble active ingredient is added to the lipid film.

The initial phospholipids are produced by processes described in the literature (DE 31 30 867 A1: Eibl et al., Chem. Phys. Lipids 28 (1981)), 1–4 41 (1986), 53–63 and 47

(1988), 47–53. It is possible here in particular to have recourse to processes described in the PCT/EP97/00749 application of 17.02.1997. Thus, the compounds according to the invention of the formula I can be prepared in the following way:

Example (A=a; n=2; m=1; y=1; z=2)

(Reaction of 1,2-dipalmitoyl-sn-glycero-3-phospho(N-methyl)ethanolamine with 1,2-isopropylidenelyceroglycidol)

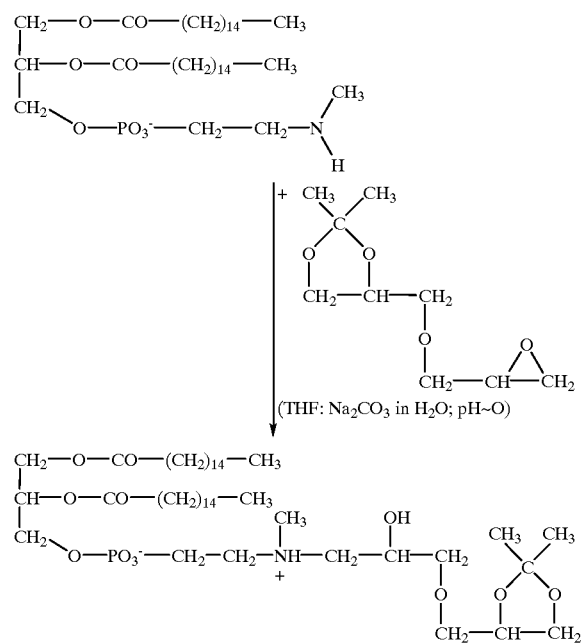

Corresponding reactions can be carried out to afford compounds with n=3–10, m=1, y=1, z=1–5. Starting compounds for x=2 and 3 are cephalins and N-methylcephalins, whose preparation has been described in detail. The reactions with the corresponding glycidols, whose preparation is described in the German patent application "Phosphatidyloligoglycerine" 19622224, leads to the required products, the addition being carried out in a 2-phase system of THF-$Na_2CO_3$/$NaHCO_3$ 1:1 (0.5 M in $H_2O$; pH 9–10). However, no hydrolysis of the fatty acid esters is observed at these pH values.

To prepare the dioleoyl compounds it is necessary to prepare 1,2-dioleoyl-sn-glycero-3-phospho-(N-methyl) ethanolamine. This is achieved by the following reaction scheme:

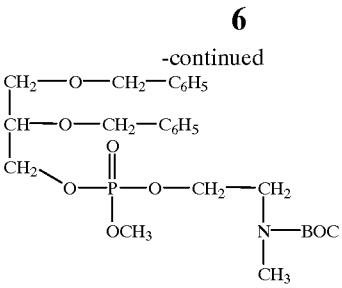

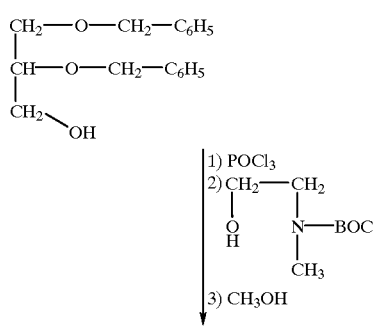

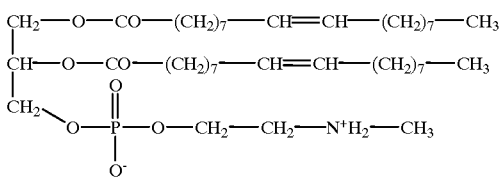

Unsaturated compounds are generally prepared analogously.

It is possible correspondingly to prepare compounds with n=4–8 because the corresponding terminal alkanolamines can be purchased and can be converted into the N-BOC-protected compounds.

Examples of a synthesis of liposome constituents are described below to demonstrate the experimental breadth of the present application. It is possible, as is evident from the examples, to prepare any fatty acid ester and alkyl ether combinations which vary in chain length, number of cis double bonds and degree of branching.

The RF values of the exemplary compounds 1 to 279 were determined in the system $CHCl_3$/$CH_3OH$/glacial acetic acid/$H_2O$=100/60/20/5 parts by volume. They are grouped very close together, specifically as follows:

| RF | Compound No. |
|---|---|
| 0.10–0.15 | 129–135 |
| 0.15–0.20 | 117–128, 167, 172, 209–216 |
| 0.20–0.25 | 70–84, 98–116, 151–166, 197–208 |
| 0.25–0.30 | 45–69, 136–150, 183–196, 262–272 |
| 0.30–0.35 | 25–44, 173–182, 255–261, 273–279 |
| 0.35–0.40 | 1–24 |
| 0.40–0.45 | 85–97 |
| 0.30–0.40 | 217–240 |
| 0.20–0.30 | 241–254 |

EXAMPLES

A) Preparation of erucoyl-1,3-propanediol-phospho-N,N,N-trimethylpropylammonium (Example 176)

Erucoyl-1,3-propanediol 1,3-Propanediol, 153 g (MW 76.1; 2 mol) is dissolved in 1 l of THF and, after addition of 60 g of triethylamine (MW 101.2, 0.6 mol) and 7.3 g of 4-dimethylaminopyridine (MW 122.2, 0.06 mol), equilibrated at 200° C. in a water bath. While stirring continuously, 178 g of erucoyl chloride (MW 357.0; 0.5 mol) in 500 ml of THF are slowly added dropwise so that the temperature in the reaction mixture does not exceed 30° C. The dropwise addition is followed by warming at 30° C. for 30 minutes and then addition of 1.5 l of diisopropyl ether and 1.5 l of 1N HCl. After vigorous shaking and phase separation, the upper ether phase is washed once again with 1% NaCl solution and evaporated in vacuo at 45° C. The residue is taken up in 2 l of hexane and cooled to −20° C. The white crystals are filtered off with suction and dried in vacuo. The yield of pure erucoyl-1,3-propanediol is 123 g (MW 396.7; 62%). The substance is pure by thin-layer chromatography (Rf value 0.3 in ether/pentane/acetic acid 200/200/2 parts by volume).

Microanalysis $C_{29}H_{45}O_3$ calc.: C, 75.70; H, 12.20; O, 12.10. found: C, 75.81; H, 12.16; =, −.

Erucoyl-1,3-propanediol-phospho-N-methylpropylammonium

Phosphorus oxychloride, 24.2 g (MW 153.33; 0.16 mol) in 15 ml of THF is cooled to 0° C. in an ice bath. A solution of erucoyl-1,3-propanediol, 60 g (MW 396.7; 0.15 mol) and 17.2 g of triethylamine (MW 101.19; 0.17 mol) in 250 ml of THF is added dropwise with stirring so that the temperature in the reaction mixture does not exceed 15° C. After the dropwise addition of the solution, the temperature of the reaction mixture is brought to 20° C. and stirred for a further 30 minutes.

The conversion of the formed erucoyl-1,3 -propanediol-phosphoric acid dichloride into the target product takes place by reaction with N-methylpropanolamine via an intermediate six-membered ring. This is done by adding a solution of 16 g of N-methylpropanolamine (MW 89.14; 0.18 mol) and 35.4 g of triethylamine (MW 101.19; 0.35 mol) in 250 ml of THF dropwise to the stirred reaction mixture in such a way that the temperature does not exceed 35° C. After the dropwise addition, the reaction mixture is kept at 25° C. for 30 minutes. The precipitated triethylamine hydrochloride is filtered off. The filtrate contains the intermediate (Rf 0.25 in $CHCl_3$/ethyl acetate 1:1, parts by volume) and is converted by adding 60 ml of 2 N HCl with ring opening into erucoyl-1,3-propanediol-phospho-N-methylpropylammonium (Rf 0.45 in $CHCl_3/CH_3OH$/glacial acetic acid/$H_2O$ 100/80/10/5, parts by volume). The THF solution of the product is mixed with 200 ml of 0.2 M sodium phosphate solution (pH~8.0) and adjusted to pH 6–7. The product is precipitated by adding 1 l of acetone, and the crystals are isolated by filtration with suction at 4° C. Erucoyl-1,3-propanediol-phospho-N-methylpropylammonium is sometimes slightly impure. Chromatography on silica gel with $CHCl_3/CH_3OH/H_2O$ can be employed for purification. The yield of pure product—based on erucoyl-1,3-propanediol—is 65 g (MW 547.8; 79%).

Microanalysis $C_{29}H_{58}NO_6P$ calc.: C, 63,59; H, 10,67; N, 2,56; O, 17,53; P, 5,66. found: C, 63,34; H, 10,49; N, 2,49; O, −; P, 5,59.

Erucoyl-1,3-propanediol-phospho-N,N,N-trimethylpropylammonium

Erucoyl-1,3-propanediol-phospho-N-methylpropylamine, 54.8 g (MW 547.8, 0.1 mol) is mixed with 800 ml of THF and 83 g of $K_2CO_3$ (0.6 mol) in 800 ml of $H_2O$. The mixture is heated to 50° C. to result in a two-phase solution. While stirring vigorously, 74.5 g of methyl toluenesulphonate (MW 186.23; 0.4 mol) in 200 ml of THF are added dropwise, and the mixture is boiled under reflux. The reaction is complete after 60 minutes. Erucoyl-1,3-propanediol-phospho-N,N,N-trimethylpropylammonium is precipitated as product (Rf value 0.1 in $CHCl_3/CH_3OH$/glacial acetic acid/$H_2O$ 100/80/10/5, parts by volume) from the THF phase with 1.2 l of acetone, and the precipitate is taken up in 300 ml of $CHCl_{13}$, filtered and again precipitated with 1.2 l of acetone. If the product is not quite pure, chromatography on silica gel with $CHCl_3/CH_3OH/H_2O$ can be employed for purification. The yield of pure product—based on the N-methyl compound—is 49 g (MW 575.8; 85%).

Microanalysis $C_{31}H_{62}NO_6P$ calc.: C, 64,66; H, 10,85; N, 2,43; O, 16,67; P, 5,38.

found: C, 64,38; H, 10,81; N, 2,39; O, −; P, 5,27.

B) Preparation of erucoyl-1,3-propanediol-phospho-N,N-dimethyl-N-(hydroxypropyldihydroxypropyl)-propylammonium

Example 155

This compound can be prepared by using the intermediate erucoyl-1,3-propanediol-phospho-N-methylpropylammonium. It is converted in a reaction firstly with an epoxide and immediately further methylated to give the final product. Erucoyl-1,3-propanediol-phospho-N-methylpropylammonium, 54.8 g (MW 547.8; 0.1 mol) is mixed with 800 ml of THF and 83 g of $K_2CO_3$ (0.6 mol) in 800 ml of $H_2O$ and heated to 50° C. to result in a two phase solution. While stirring vigorously, a solution of 21 g of 1,2-isopropylideneglycero-3,1-glycidol (MW 188.2; 0.11 mol) in 200 ml of THF is added dropwise, and the temperature is raised to 60° C. The reaction mixture is boiled under gentle reflux for 2 hours, and 37 g of methyl toluenesulphonate (MW 196.23; 0.2 mol) in 100 ml of THF are added. The reaction is complete after boiling under reflux for 2 hours. The THF phase is substantially evaporated at 45° C., and the residue is heated with 300 ml of 70% acetic acid at 60–65° C. to remove the isopropylidene protective group. A mixture of 1 l of $CHCl_3$, 1 l of $CH_3OH$ and 1 l of 1% strength NaCl solution is added to the reaction mixture and, after thorough shaking, the solvent is removed from the lower $CHCl_3$ phase in vacuo. The residue is taken up in 400 ml of $CHCl_3$ and precipitated with 1.6 l of acetone. Chromatography on silica gel with $CHCl_3/CH_3OH/H_2O$ can be employed for purification. 46 g of erucoyl-1,3-propane-diol-phospho-N,N-dimethyl-N-(hydroxy-3,1-dihydroxypropyl)propylammonium (MW 709.94; 656) are obtained.

All the compounds detailed hereinafter can be prepared by these general methods for preparing compounds both hydroxylated on the nitrogen and non-hydroxylated.

Examples of two-chain glycerophospho-N,N-dimethyl-N-dihydroxypropylalkylammonium compounds (A=a; n=2–6; $R_3$, $CH_3$; m=1; x=0; y=1; z=1)

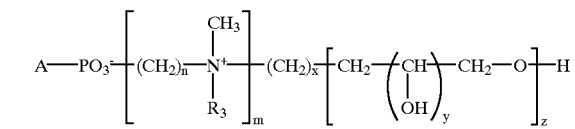

Formel I 1) 1,2-Dipalmitoyl-sn-glycero-3-phospho-N,N-dimethyl-N-dihydroxypropyl-ethylammonium (n = 2)
($R_1$, $R_2$ = CO—O$CH_2)_{14}$—$CH_3$)
$C_{42}H_{84}NO_{10}P$ (794.10)

2) 1,2-Distearoyl-sn-glycero-3-phospho-N,N-dimethyl-N-dihydroxypropyl-ethylammonium (n = 2)
($R_1$, $R_2$ = CO—$(CH_2)_{16}$—$CH_3$)
$C_{46}H_{92}NO_{10}P$ (850.20)

3) 1,2-Dimyristoyl-sn-glycero-3-phospho-N,N-dimethyl-N-dihydroxypropyl-ethylammonium (n = 2)
($R_1$, $R_2$ = CO—$(CH_2)_{12}$—$CH_3$)
$C_{38}H_{76}NO_{10}P$ (737.99)

4) 1,2-Dierucyl-sn-glycero-3-phospho-N,N-dimethyl-N-dihydroxypropyl-ethylammonium (n = 2)
($R_1$, $R_2$ = CO—$(CH_2)_{11}$—CH = CH—$(CH_2)_7$—$CH_3$)
$C_{54}H_{104}NO_{10}P$ (958.39)

5) 1,2-Dioleoyl-sn-glycero-3-phospho-N,N-dimethyl-N-dihydroxypropyl-ethylammonium (n = 2)
($R_1$, $R_2$ = CO—$(CH_2)_7$—CH = CH—$(CH_2)_7$—$CH_3$)
$C_{46}H_{88}NO_{10}P$ (846.17)

6) 1-Stearoyl-2-oleoyl-sn-glycero-3-phospho-N,N-dimethyl-N-dihydroxypropyl-ethylammonium (n = 2)
($R_1$ = CO—$(CH_2)_{16}$—$CH_3$; $R_2$ = CO—$(CH_2)_{17}$—CH = CH—$(CH_2)_2$—$CH_3$)
$C_{46}H_{90}NO_{10}P$ (848.19)

7) 1-Stearoyl-2-myristoyl-sn-glycero-3-phospho-N,N-dimethyl-N-dihydroxypropyl-ethylammonium (n = 2)
($R_1$ = CO—$(CH_2)_{16}$—$CH_3$; $R_2$ = CO—$(CH_2)_{12}$—$CH_3$)
$C_{42}H_{84}NO_{10}P$ (794.10)

8) 1-Stearoyl-2-lauroyl-sn-glycero-3-phospho-N,N-dimethyl-N-dihydroxypropyl-ethylammonium (n = 2)
($R_1$, = CO—$(CH_2)_{16}$—$CH_3$; $R_2$ = CO—$(CH_2)_{10}$—$CH_3$)
$C_{40}H_{80}NO_{10}P$ (766.04)

9) 1-Lauroyl-2-stearoyl-sn-glycero-3-phospho-N,N-dimethyl-N-dihydroxypropyl-ethylammonium (n = 2)
($R_1$ = CO—$(CH_2)_{10}$—$CH_3$; $R_2$ = CO—$(CH_2)_{16}$—$CH_3$)
$C_{40}H_{80}NO_{10}P$ (766.04)

10) 1-Erucoyl-2-oleoyl-sn-glycero-3-phospho-N,N-dimethyl-N-dihydroxypropyl-ethylammonium (n = 2)
($R_1$ = CO—$(CH_2)_{11}$—CH = CH—$(CH_2)_7$—$CH_3$)
($R_2$ = CO—$(CH_2)_7$—CH = CH—$(CH_2)_7$—$CH_3$)
$C_{50}H_{96}NO_{10}P$ (902.28)

11) 1-Oleoyl-2-erucyl-sn-glycero-3-phospho-N,N-dimethyl-N-dihydroxypropyl-ethylammonium (n = 2)
($R_1$ = CO—$(CH_2)_7$—CH = CH—$(CH_2)_7$—$CH_3$)
($R_2$ = CO—$(CH_2)_{11}$—CH = CH—$(CH_2)_7$—$CH_3$)
$C_{50}H_{96}NO_{10}P$ (902.28)

12) 1,2-Dipalmitoyl-sn-glycero-3-phospho-N,N-dimethyl-N-dihydroxypropyl-ethylammonium (n = 3)
($R_1$, $R_2$ = Cl—$(CH_2)_{14}$—$CH_3$)
$C_{43}H_{86}NO_{10}P$ (808.12)

13) 1,2-Dierucyl-sn-glycero-3-phospho-N,N-dimethyl-N-dihydroxypropyl-ethylammonium (n = 3)
($R_1$, $R_2$ = CO—$(CH_2)_{11}$—CH = CH—$(CH_2)_7$—$CH_3$)
$C_{55}H_{106}NO_{10}P$ (972.413)

14) 1,2-Dioleoyl-sn-glycero-3-phospho-N,N-dimethyl-N-dihydroxypropyl-ethylammonium (n = 3)
($R_1$, $R_2$ = CO—$(CH_2)_7$—CH = CH—$(CH_2)_7$—$CH_3$)
$C_{47}H_{90}NO_{10}P$ (860.20)

15) 1-stearoyl-2-oleoyl-sn-glycero-3-phospho-N,N-dimethyl-N-dihydroxypropyl-ethylammonium (n = 3)
($R_1$ = CO—$(CH_2)_{16}$—$CH_3$; $R_2$= CO—$(CH_2)_7$—CH = CH—$(CH_2)_7$—$CH_3$)
$C_{47}H_{92}NO_{10}P$ (862.21)

16) 1-Stearoyl-2-lauroyl-sn-glycero-3-phospho-N,N-dimethyl-N-dihydroxypropyl-ethylammonium (n = 3)
($R_1$ = CO—$(CH_2)_{16}$—$CH_3$; $R_2$ = CO—$(CH_2)_{10}$—$CH_3$)
$C_{41}H_{82}NO_{10}P$ (780.07)

17) 1,2-Dipalmitoyl-sn-glycero-3-phospho-N,N-dimethyl-N-dihydroxypropyl-butylammonium (n = 4)
($R_1$, $R_2$ = CO—$(CH_2)_{14}$—$CH_3$)
$C_{44}H_{88}NO_{10}P$ (822.15)

18) 1,2-Dioleoyl-sn-glycero-3-phospho-N,N-dimethyl-N-dihydroxypropyl-butylammonium (n = 4)
($R_1$, $R_2$ = CO—$(CH_2)_7$—CH = CH—$(CH_2)_7$—$CH_3$)
$C_{48}H_{92}NO_{10}P$ (874.23)

19) 1,2-Dierucyl-sn-glycero-3-phospho-N,N-dimethyl-N-dihydroxypropyl-butylammonium (n = 4)
($R_1$, $R_2$ = CO—$(CH_2)_7$—CH = CH—$(CH_2)_7$—$CH_3$)
$C_{56}H_{108}NO_{10}P$ (986.44)

20) 1-Stearoyl-2-oleoyl-sn-glycero-3-phospho-N,N-dimethyl-N-dihydroxypropyl-butylammonium (n = 4)
($R_1$ = CO—$(CH_2)_{16}$—$CH_3$; $R_2$ = CO—$(CH_2)_7$—CH = CH—$(CH_2)_7$—$CH_3$)
$C_{48}H_{94}NO_{10}P$ (876.24)

21) 1-Stearoyl-2-lauroyl-sn-glycero-3-phospho-N,N-dimethyl-N-dihydroxypropyl-butylammonium (n = 4)
($R_1$ = CO—$(CH_2)_{16}$—$CH_3$; $R_2$ = CO—$(CH_2)_{10}$—$CH_3$)
$C_{42}H_{84}NO_{10}P$ (794.10)

22) 1,2-Dipalmitoyl-sn-glycero-3-phospho-N,N-dimethyl-N-dihydroxypropyl-hexylammonium (n = 6)
$R_1$, $R_2$ = CO—$(CH_2)_{14}$—$CH_3$)
$C_{42}H_{84}NO_{10}P$ (794.10)

23) 1,2-Dioleoyl-sn-glycero-3-phospho-N,N-dimethyl-N-dihydroxypropyl-hexylammonium (n = 6)
($R_1$, $R_2$ = CO—$(CH_2)_7$—CH = CH—$(CH_2)_7$—$CH_3$)
$C_{50}H_{96}NO_{10}P$ (902.28)

24) 1,2-Dierucyl-sn-glycero-3-phospho-N,N-dimethyl-N-dihydroxypropyl-hexylammonium (n = 6)
($R_1$, $R_2$ = CO—$(CH_2)_{11}$—CH = CH—$(CH_2)_7$—$CH_3$)
$C_{56}H_{112}NO_{10}P$ (1014.49)

Examples of two-chain glycerophospho-N,N-dimethyl-N-(2-hydroxypropyl-3,1-O,O-dihydroxypropyl)alkylammonium compounds (A=a; n=2–6; $R_3$, $O_3$; m=1; x=O; y=1; z=2)

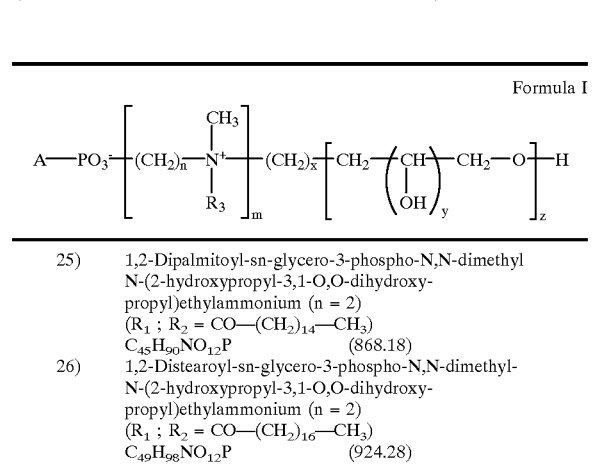

Formula I 25) 1,2-Dipalmitoyl-sn-glycero-3-phospho-N,N-dimethyl N-(2-hydroxypropyl-3,1-O,O-dihydroxypropyl)ethylammonium (n = 2)
($R_1$ ; $R_2$ = CO—$(CH_2)_{14}$—$CH_3$)
$C_{45}H_{90}NO_{12}P$ (868.18)

26) 1,2-Distearoyl-sn-glycero-3-phospho-N,N-dimethyl-N-(2-hydroxypropyl-3,1-O,O-dihydroxypropyl)ethylammonium (n = 2)
($R_1$ ; $R_2$ = CO—$(CH_2)_{16}$—$CH_3$)
$C_{49}H_{98}NO_{12}P$ (924.28)

-continued

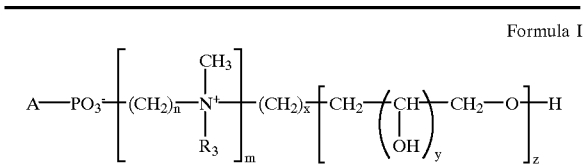
Formula I 27) 1,2-Dierucoyl-sn-glycero-3-phospho-N,N-dimethyl-N-(2-hydroxypropyl-3,1-O,O-dihydroxypropyl)-ethylammonium (n = 2)
($R_1$; $R_2$ = CO—$(CH_2)_{11}$—CH = CH—$(CH_2)_7$—$CH_3$)
$C_{57}H_{110}NO_{12}P$ (1032.47)

28) 1,2-Dioleoyl-sn-glycero-3-phospho-N,N-dimethyl-N-(2-hydroxypropyl-3,1-O,O-dihydroxypropyl) ethylammonium (n = 2)
($R_1$; $R_2$ = CO—$(CH_2)_7$—CH = CH—$(CH_2)_7$—$CH_2$)
$C_{49}H_{94}NO_{12}P$ (920.25)

29) 1-Stearoyl-2-oleoyl-sn-glycero-3-phospho-N,N-dimethyl-N-(2-hydroxypropyl-3,1-O,O-dihydroxypropyl)ethylammonium (n = 2)
($R_1$ = CO—$(CH_2)_{16}$—$CH_3$; $R_2$ = CO—$(CH_2)_7$—CH = CH—$(CH_2)_7$—$CH_3$)
$C_{49}H_{96}NO_{12}P$ (922.27)

30) 1-Stearoyl-2-lauroyl-sn-glycero-3-phospho-N,N-dimethyl-N-(2-hydroxypropyl-3,1-O,O-dihydroxypropyl)ethylammonium (n = 2)
($R_1$ = CO—$(CH_2)_{16}$—$CH_3$; $R_2$ = CO—$(CH_2)_{10}$—$CH_3$)
$C_{43}H_{86}NO_{12}P$ (840.12)

31) 1-Erucoyl-2-oleoyl-sn-glycero-3-phospho-N,N-dimethyl-N-(2-hydroxypropyl-3,1-O,O-dihydroxypropyl)ethylammonium (n = 2)
($R_2$ = CO—$(CH_2)_{11}$—CH = CH—$(CH_2)_7$—$CH_3$; $R_2$ = CO—$(CH_2)_7$—CH = CH—$(CH_2)_7$—$CH_3$)
$C_{53}H_{102}NO_{12}P$ (976.36)

32) 1-Oleoyl-2-erucoyl-sn-glycero-3-phospho-N,N-dimethyl-N-(2-hydroxypropyl-3,1-O,O-dihydroxypropyl)ethylammonium (n = 2)
($R_1$ = CO—$(CH_2)_7$—CH = CH—$(CH_2)_7$—$CH_3$; $R_2$ = CO—$(CH_2)_{11}$—CH = CH—$(CH_2)_7$—$CH_3$)
$C_{53}H_{102}NO_{12}P$ (976.36)

33) 1,2-Dipalmitoyl-sn-glycero-3-phospho-N,N-dimethyl-N-(2-hydroxypropyl-3,1-O,O-dihydroxypropyl)propylammonium (n = 3)
($R_1$, $R_2$ = CO—$(CH_2)_{14}$—$CH_3$)
$C_{46}H_{92}NO_{12}P$ (882.20)

34) 1,2-Distearoyl-sn-glycero-3-phospho-N,N-dimethyl-N-(2-hydroxypropyl-3,1-O,O-dihydroxypropyl)propylammonium (n = 3)
($R_1$, $R_2$ = CO—$(CH_2)_{16}$—$CH_3$)
$C_{50}H_{100}NO_{12}P$ (938.31)

35) 1,2-Dierucoyl-sn-glycero-3-phospho-N,N-dimethyl-N-(2-hydroxypropyl-3,1-O,O-dihydroxypropyl)propylammonium (n = 3)
($R_1$, $R_2$ = CO—$(CH_2)_{11}$—CH = CH—$(CH_2)_7$—$CH_3$)
$C_{58}H_{112}NO_{12}P$ (1046.49)

36) 1,2-Dioleoyl-sn-glycero-3-phospho-N,N-dimethyl-N-(2-hydroxypropyl-3,1-O,O-dihydroxypropyl)-propylammonium (n = 3)
($R_1$, $R_2$ = CO—$(CH_2)_7$—CH = CH—$(CH_2)_7$—$CH_3$)
$C_{50}H_{96}NO_{12}P$ (934.28)

37) 1-Stearoyl-2-oleoyl-sn-glycero-3-phospho-N,N-dimethyl-N-(2-hydroxypropyl-3,1-O,O-dihydroxypropyl)propylammonium (n = 3)
($R_1$ = CO—$(CH_2)_{16}$—$CH_3$; $R_2$ = CO—$(CH_2)_7$—CH = CH—$(CH_2)_7$—$CH_3$)
$C_{50}H_{96}NO_{12}P$ (936.29)

38) 1-Stearoyl-2-lauroyl-sn-glycero-3-phospho-N,N-dimethyl-N-(2-hydroxypropyl-3,1-O,O-dihydroxypropyl)propylammonium (n = 3)
($R_1$ = CO—$(CH_2)_{16}$—$CH_3$; $R_2$ = CO—$(CH_2)_{10}$—$CH_3$)
$C_{44}H_{88}NO_{12}P$ (854.15)

39) 1,2-Dioleoyl-sn-glycero-3-phospho-N,N-dimethyl-N-(2-hydroxypropyl-3,1-O,O-dihydroxypropyl)butylammonium (n = 4)
($R_1$, $R_2$ = CO—$(CH_2)_7$—CH = CH—$(CH_2)_7$—$CH_3$)
$C_{51}H_{98}NO_{12}P$ (948.30)

40) 1,2-Dierucoyl-sn-glycero-3-phospho-N,N-dimethyl-N-(2-hydroxypropyl-3,1-O,O-dihydroxypropyl) butylammonium (n = 4)
($R_1$, $R_2$ = CO—$(CH_2)_{11}$—CH = CH—$(CH_2)_7$—$CH_3$)
$C_{69}H_{114}NO_{12}P$ (1060.52)

41) 1-Stearoyl-2-oleoyl-sn-glycero-3-phospho-N,N-dimethyl-N-(2-hydroxypropyl-3,1-O,O-dihydroxypropyl)butylammonium (n = 4)
($R_1$ = CO—$(CH_2)_{16}$—$CH_3$; $R_2$ = CO—$(CH_2)_7$—CH = CH—$(CH_2)_7$—$CH_3$)
$C_{51}H_{100}NO_{12}P$ (950.32)

42) 1-Stearoyl-2-lauroyl-sn-glycero-3-phospho-N,N-dimethyl-N-(2-hydroxypropyl-3,1-O,O-dihydroxypropyl)butylammonium (n = 4)
($R_1$ = CO—$(CH_2)_{16}$—$CH_3$; $R_2$ = CO—$(CH_2)_{10}$—$CH_3$)
$C_{45}H_{90}NO_{12}P$ (868.175)

43) 1,2-Dioleoyl-sn-glycero-3-phospho-N,N-dimethyl-N-(2-hydroxypropyl-3,1-O,O-dihydroxypropyl)hexylammonium (n = 6)
($R_1$, $R_2$ = CO—$(CH_2)_7$—CH = CH—$(CH_2)_7$—$CH_3$)
$C_{53}H_{102}NO_{12}P$ (976.358)

44) 1,2-Dierucoyl-sn-glycero-3-phospho-N,N-dimethyl-N-(2-hydroxypropyl-3,1-O,O-dihydroxypropyl)hexylammonium (n = 6)
($R_1$, $R_2$ = CO—$(CH_2)_{11}$—CH = CH—$(CH_2)_7$—$CH_3$)
$C_{61}H_{118}NO_{12}P$ (1088.57)

Examples of two-chain glycerophospho-N,N-dimethyl-N-(2-hydroxypropyl-3,1-O,O-2-hydroxypropyl-3,1-O,O-dihydroxypropyl) alkylammonium compounds (A =a; n=2–8; $R_3$, $CH_3$; m=1; x=O; y=1; z=3)

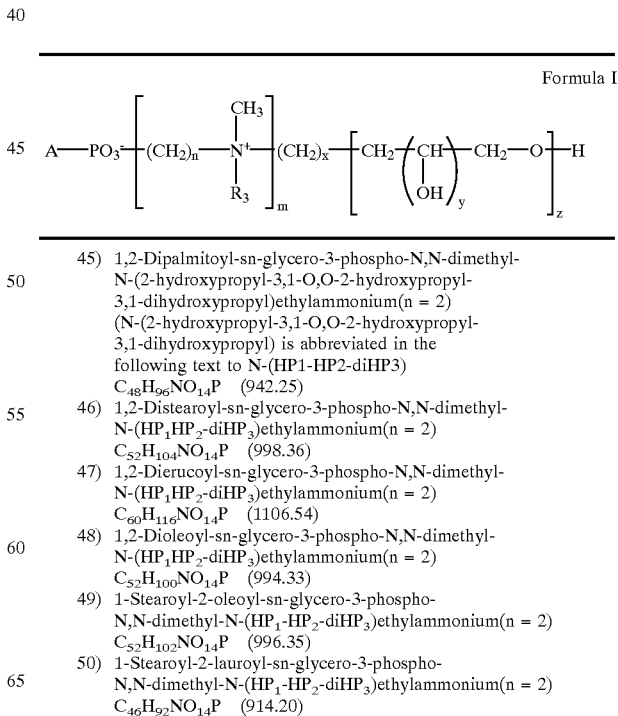
Formula I 45) 1,2-Dipalmitoyl-sn-glycero-3-phospho-N,N-dimethyl-N-(2-hydroxypropyl-3,1-O,O-2-hydroxypropyl-3,1-dihydroxypropyl)ethylammonium(n = 2)
(N-(2-hydroxypropyl-3,1-O,O-2-hydroxypropyl-3,1-dihydroxypropyl) is abbreviated in the following text to N-(HP1-HP2-diHP3)
$C_{48}H_{96}NO_{14}P$ (942.25)

46) 1,2-Distearoyl-sn-glycero-3-phospho-N,N-dimethyl-N-(HP$_1$HP$_2$-diHP$_3$)ethylammonium(n = 2)
$C_{52}H_{104}NO_{14}P$ (998.36)

47) 1,2-Dierucoyl-sn-glycero-3-phospho-N,N-dimethyl-N-(HP$_1$HP$_2$-diHP$_3$)ethylammonium(n = 2)
$C_{60}H_{116}NO_{14}P$ (1106.54)

48) 1,2-Dioleoyl-sn-glycero-3-phospho-N,N-dimethyl-N-(HP$_1$HP$_2$-diHP$_3$)ethylammonium(n = 2)
$C_{52}H_{100}NO_{14}P$ (994.33)

49) 1-Stearoyl-2-oleoyl-sn-glycero-3-phospho-N,N-dimethyl-N-(HP$_1$-HP$_2$-diHP$_3$)ethylammonium(n = 2)
$C_{52}H_{102}NO_{14}P$ (996.35)

50) 1-Stearoyl-2-lauroyl-sn-glycero-3-phospho-N,N-dimethyl-N-(HP$_1$-HP$_2$-diHP$_3$)ethylammonium(n = 2)
$C_{46}H_{92}NO_{14}P$ (914.20)

-continued

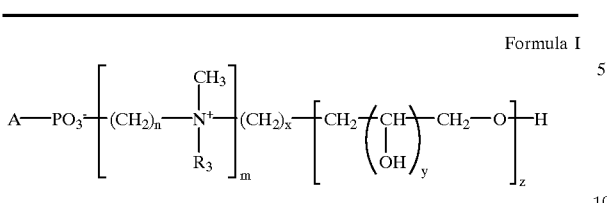

Formula I 51) 1,2-Palmitoyl-2-lauroyl-sn-glycero-3-phospho-N,N-dimethyl-N-(HP$_1$HP$_2$-diHP$_3$)ethylammonium(n = 2)
$C_{44}H_{88}NO_{14}P$  (886.15)
52) 1,2-Dipalmitoyl-sn-glycero-3-phospho-N,N-dimethyl-N-(HP$_1$HP$_2$-diHP$_3$)propylammonium(n = 3)
$C_{49}H_{98}NO_{14}P$  (956.28)
53) 1,2-Distearoyl-sn-glycero-3-phospho-N,N-dimethyl-N-(HP$_1$HP$_2$-diHP$_3$)propylammonium(n = 3)
$C_{53}H_{106}NO_{14}P$  (1012.39)
54) 1,2-Dierucoyl-sn-glycero-3-phospho-N,N-dimethyl-N-(HP$_1$-HP$_2$-diHP$_3$)propylammonium(n = 3)
$C_{61}H_{118}NO_{14}P$  (1120.57)
55) 1,2-Dioleoyl-sn-glycero-3-phospho-N,N-dimethyl-N-(HP$_1$HP$_2$-diHP$_3$)propylammonium(n = 3)
$C_{53}H_{102}NO_{14}P$  (1008.36)
56) 1-Stearoyl-2-oleoyl-sn-glycero-3-phospho-N,N-dimethyl-N-(HP$_1$-HP$_2$-diHP$_3$)propylammonium(n = 3)
$C_{53}H_{104}NO_{14}P$  (1010.37)
57) 1-Stearoyl-2-lauroyl-sn-glycero-3-phospho-N,N-dimethyl-N-(HP$_1$-HP$_2$-diHP$_3$)propylammonium(n = 3)
$C_{47}H_{94}NO_{14}P$  (928.23)
58) 1-Palmitoyl-2-lauroyl-sn-glycero-3-phospho-N,N-dimethyl-N-(HP$_1$-HP$_2$-diHP$_3$)propylammonium(n = 3)
$C_{45}H_{90}NO_{14}P$  (900.17)
59) 1,2-Dipalmitoyl-sn-glycero-3-phospho-N,N-dimethyl-N-(HP$_1$HP$_2$-diHP$_3$)butylammonium(n = 4)
$C_{50}H_{100}NO_{14}P$  (970.31)
60) 1,2-Distearoyl-sn-glycero-3-phospho-N,N-dimethyl-N-(HP$_1$HP$_2$-diHP$_3$)butylammonium(n = 4)
$C_{54}H_{108}NO_{14}P$  (1026.41)
61) 1,2-Dierucoyl-sn-glycero-3-phospho-N,N-dimethyl-N-HP$_1$-HP$_2$-diHP$_3$)butylammonium(n = 4)
$C_{62}H_{120}NO_{14}P$  (1134.60)
62) 1,2-Dioleoyl-sn-glycero-3-phospho-N,N-dimethyl-N-(HP$_1$-HP$_2$-diHP$_3$)butylammonium(n = 4)
$C_{54}H_{104}NO_{14}P$  (1022.38)
63) 1,2-Dipalmitoyl-sn-glycero-3-phospho-N,N-dimethyl-N-(HP$_1$-HP$_2$-diHP$_3$)hexylammonium(n = 6)
$C_{52}H_{104}NO_{14}P$  (998.36)
64) 1,2-Distearoyl-sn-glycero-3-phospho-N,N-dimethyl-N-(HP$_1$-HP$_2$-diHP$_3$)hexylammonium(n = 6)
$C_{56}H_{112}NO_{14}P$  (1054.47)
65) 1,2-Dierucoyl-sn-glycero-3-phospho-N,N-dimethyl-N-(HP$_1$HP$_2$-diHP$_3$)hexylammonium(n = 6)
$C_{64}H_{124}NO_{14}P$  (1162.65)
66) 1,2-Dioleoyl-sn-glycero-3-phospho-N,N-dimethyl-N-(HP$_1$-HP$_2$-diHP$_3$)hexylammonium(n = 6)
$C_{56}H_{108}NO_{14}P$  (1050.44)
67) 1,2-Distearoyl-sn-glycero-3-phospho-N,N-dimethyl-N-(HP$_1$HP$_2$-diHP$_3$)octylammonium(n = 8)
$C_{58}H_{116}NO_{14}P$  (1082.52)
68) 1,2-Dioleoyl-sn-glycero-3-phospho-N,N-dimethyl-N-(HP$_1$-HP$_2$-diHP$_3$)octylammonium(n = 8)
$C_{58}H_{112}NO_{14}P$  (1078.49)
69) 1,2-Dierucoyl-sn-glycero-3-phospho-N,N-dimethyl-N-(HP$_1$HP$_2$-diHP$_3$)octylammonium(n = 8)
$C_{66}H_{128}NO_{14}P$  (1190.70)

Examples of two-chain glycerophospho-N,N-dimethyl-N-(2-hydroxypropyl-3,1-O,O-2-hydroxypropyl-3,1-O,O-2-hydroxypropyl-3,1-O,O-dihydroxypoxmropyl)alkylammonium compounds (A=a: n=2,3; R$_3$, O$_3$; m=1; x=0, y=1; z=4)

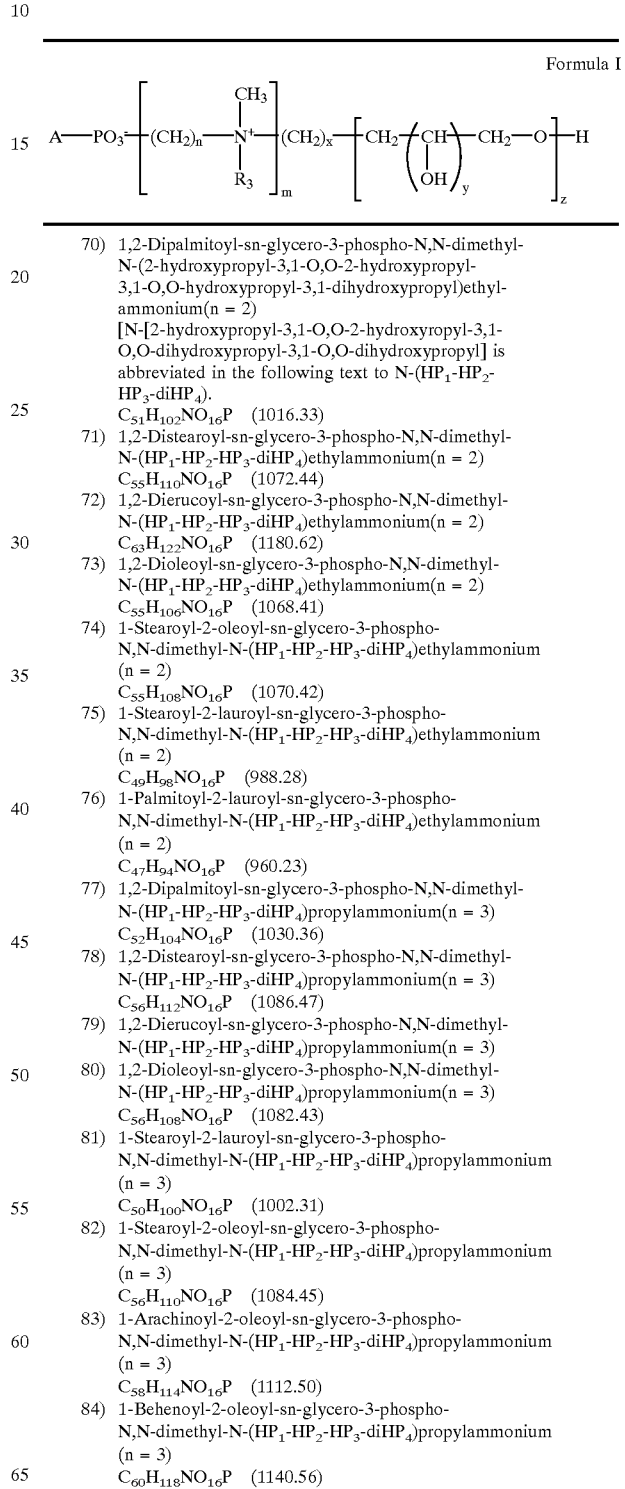

Formula I 70) 1,2-Dipalmitoyl-sn-glycero-3-phospho-N,N-dimethyl-N-(2-hydroxypropyl-3,1-O,O-2-hydroxypropyl-3,1-O,O-hydroxypropyl-3,1-dihydroxypropyl)ethyl-ammonium(n = 2)
[N-[2-hydroxypropyl-3,1-O,O-2-hydroxyropyl-3,1-O,O-dihydroxypropyl-3,1-O,O-dihydroxypropyl] is abbreviated in the following text to N-(HP$_1$-HP$_2$-HP$_3$-diHP$_4$).
$C_{51}H_{102}NO_{16}P$  (1016.33)
71) 1,2-Distearoyl-sn-glycero-3-phospho-N,N-dimethyl-N-(HP$_1$-HP$_2$-HP$_3$-diHP$_4$)ethylammonium(n = 2)
$C_{55}H_{110}NO_{16}P$  (1072.44)
72) 1,2-Dierucoyl-sn-glycero-3-phospho-N,N-dimethyl-N-(HP$_1$-HP$_2$-HP$_3$-diHP$_4$)ethylammonium(n = 2)
$C_{63}H_{122}NO_{16}P$  (1180.62)
73) 1,2-Dioleoyl-sn-glycero-3-phospho-N,N-dimethyl-N-(HP$_1$-HP$_2$-HP$_3$-diHP$_4$)ethylammonium(n = 2)
$C_{55}H_{106}NO_{16}P$  (1068.41)
74) 1-Stearoyl-2-oleoyl-sn-glycero-3-phospho-N,N-dimethyl-N-(HP$_1$-HP$_2$-HP$_3$-diHP$_4$)ethylammonium (n = 2)
$C_{55}H_{108}NO_{16}P$  (1070.42)
75) 1-Stearoyl-2-lauroyl-sn-glycero-3-phospho-N,N-dimethyl-N-(HP$_1$-HP$_2$-HP$_3$-diHP$_4$)ethylammonium (n = 2)
$C_{49}H_{98}NO_{16}P$  (988.28)
76) 1-Palmitoyl-2-lauroyl-sn-glycero-3-phospho-N,N-dimethyl-N-(HP$_1$-HP$_2$-HP$_3$-diHP$_4$)ethylammonium (n = 2)
$C_{47}H_{94}NO_{16}P$  (960.23)
77) 1,2-Dipalmitoyl-sn-glycero-3-phospho-N,N-dimethyl-N-(HP$_1$-HP$_2$-HP$_3$-diHP$_4$)propylammonium(n = 3)
$C_{52}H_{104}NO_{16}P$  (1030.36)
78) 1,2-Distearoyl-sn-glycero-3-phospho-N,N-dimethyl-N-(HP$_1$-HP$_2$-HP$_3$-diHP$_4$)propylammonium(n = 3)
$C_{56}H_{112}NO_{16}P$  (1086.47)
79) 1,2-Dierucoyl-sn-glycero-3-phospho-N,N-dimethyl-N-(HP$_1$-HP$_2$-HP$_3$-diHP$_4$)propylammonium(n = 3)
80) 1,2-Dioleoyl-sn-glycero-3-phospho-N,N-dimethyl-N-(HP$_1$-HP$_2$-HP$_3$-diHP$_4$)propylammonium(n = 3)
$C_{56}H_{108}NO_{16}P$  (1082.43)
81) 1-Stearoyl-2-lauroyl-sn-glycero-3-phospho-N,N-dimethyl-N-(HP$_1$-HP$_2$-HP$_3$-diHP$_4$)propylammonium (n = 3)
$C_{50}H_{100}NO_{16}P$  (1002.31)
82) 1-Stearoyl-2-oleoyl-sn-glycero-3-phospho-N,N-dimethyl-N-(HP$_1$-HP$_2$-HP$_3$-diHP$_4$)propylammonium (n = 3)
$C_{56}H_{110}NO_{16}P$  (1084.45)
83) 1-Arachinoyl-2-oleoyl-sn-glycero-3-phospho-N,N-dimethyl-N-(HP$_1$-HP$_2$-HP$_3$-diHP$_4$)propylammonium (n = 3)
$C_{58}H_{114}NO_{16}P$  (1112.50)
84) 1-Behenoyl-2-oleoyl-sn-glycero-3-phospho-N,N-dimethyl-N-(HP$_1$-HP$_2$-HP$_3$-diHP$_4$)propylammonium (n = 3)
$C_{60}H_{118}NO_{16}P$  (1140.56)

Examples of two-chain glycerophospho compounds not hydroxylated on the nitrogen (A=a; n=2–6; m=1; x=1; z=0)

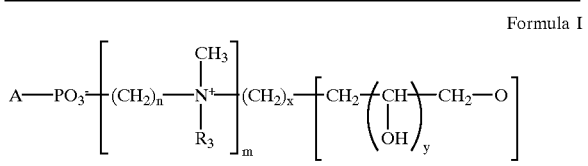

Formula I 85) 1,2-Dioleoyl-sn-glycero-3-phospho-N,N,N-trimethyl-propylammonium
$C_{45}H_{86}NO_8P$ (800.15)
86) 1,2-Dioleoyl-sn-glycero-3-phospho-N,N,N-trimethyl-butylammonium
$C_{46}H_{88}NO_8P$ (814.17)
87) 1,2-Dioleoyl-sn-glycero-3-phospho-N,N,N-trimethyl-pentylammonium
$C_{47}H_{90}NO_8P$ (828.20)
88) 1,2-Dioleoyl-sn-glycero-3-phospho-N,N,N-trimethyl-hexyl ammonium
$C_{48}H_{92}NO_8P$ (842.23)
89) 1-Stearoyl-2-oleoyl-sn-glycero-3-phospho-N,N,N-trimethylpropylammonium
$C_{45}H_{88}NO_8P$ (802.16)
90) 1-Stearoyl-2-oleoyl-sn-glycero-3-phospho-N,N,N-trimethylbutylammonium
$C_{46}H_{90}NO_8P$ (816.19)
91) 1-Palmitoyl-2-lauroyl-sn-glycero-3-phospho-N,N,N-trimethylpropylammonium
$C_{37}H_{74}NO_8P$ (691.97)
92) 1-Oleoyl-2-lauroyl-sn-glycero-3-phospho-N,N,N-trimethylpropylammonium
$C_{39}H_{76}NO_8P$ (718.00)
93) 1-Erucoyl-2-oleoyl-sn-glycero-3-phospho-N,N,N-trimethylpropylammonium
$C_{49}H_{94}NO_8P$ (856.26)
94) 1-Erucoyl-2-oleoyl-sn-glycero-3-phospho-N,N,N-trimethylbutylammonium
$C_{50}H_{96}NO_8P$ (870.28)
95) 1-Erucoyl-2-oleoyl-sn-glycero-3-phospho-N,N,N-trimethylhexylammonium
$C_{52}H_{100}NO_8P$ (898.34)
96) 1-Nervonoyl-2-lauroyl-sn-glycero-3-phospho-N,N,N-trimethylpropylammonium
$C_{45}H_{88}NO_8P$ (802.16)
97) 1-Nervonoyl-2-oleoyl-sn-glycero-3-phospho-N,N,N-trimethylpropylammonium
$C_{51}H_{98}NO_8P$ (884.31)

2) Solubilizers

It has emerged that certain substances from the compounds presented herein, especially those which are soluble in ethanol, are excellent solubilizers for substances of low solubility in water. Thus, for example, Taxol can be converted in a simple manner into a form which can be administered intravenously. Likewise, for example Taxotere, cyclosporin, cholesterol and derivatives thereof, steroids, cortisone and analogues, erucylphosphocholine (dissolving of the gel-like structures) have proved to be readily soluble.

In particular, substances which have proved useful for this are those having a distance of 3 C. atoms between phosphate and ammonium (n=3 in the general formula I), for example the substances from Examples 14, 85, 111, 139, 144, 176. Outstandingly suitable for these purposes is a simple substance 1-erucoyl-1,3-propane-diol-phospho-N,N,N-trimethylpropylammonium (176). This substance can be prepared simply and in high yields on the tonnage scale.

The solubilizers are preferably single-chain compounds, that is to say when A=a one of $R_1$ and $R_2$ is hydrogen or an alkyl with 1 to 3 C. atoms.

Taxol for Intravenous Administration

A solution is prepared from 0.3 g of Taxol and 1.75 g of substance No. 176 in 7.95 g of absolute ethanol. The solution is sterilized by filtration and stored at 4° C. until used.

For intravenous administration, the stock solution is diluted 1:10 or 1:100 with physiological saline.

Examples of single-chain glycerophospho-N,N-dimethyl-N-dihydroxypropylalkylammonium compounds (A=a; n=2–6; $R_3$, $CH_3$; m=1,x=0, y=1,z=1)

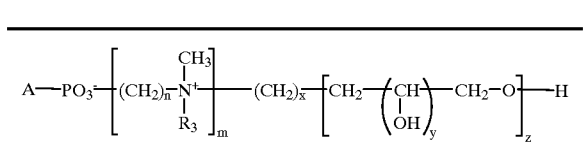

98) 1-Palmitoyl-sn-glycero-3-phospho-N,N-dimethyl-N-(diHP)-ethylammonium (n = 2)
$C_{26}H_{54}NO_9P$ (555.69)
99) 1-Stearoyl-sn-glycero-3-phospho-N,N-dimethyl-N-(diHP)-ethylammonium (n = 2)
$C_{28}H_{58}NO_9P$ (583.74)
100) 1-Arachinoyl-sn-glycero-3-phospho-N,N-dimethyl-N-(diHP)-ethylammonium (n = z)
$C_{30}H_{62}NO_9P$ (611.79)
101) 1-Behenoyl-sn-glycero-3-phospho-N,N-dimethyl-N-(diHP)-ethylammonium (n = 2)
$C_{32}H_{66}NO_9P$ (639.85)
102) 1-Erucoyl-sn-glycero-3-phospho-N,N-dimethyl-N-(diHP)-ethylammonium (n = 2)
$C_{32}H_{64}NO_9P$ (637.83)
103) 1-Nervonoyl-sn-glycero-3-phospho-N,N-dimethyl-N-(diHP)-ethylammonium (n = 2)
$C_{34}H_{68}NO_9P$ (665.88)
104) 1-0-Hexadecyl-sn-glycero-3-phospho-N,N-dimethyl-N-(diHP)-ethylammonium (n = 2)
105) 1-0-Octadecyl-sn-glycero-3-phospho-N,N-dimethyl-N-(diHP)-ethylammonium (n = 2)
$C_{28}H_{60}NO_8P$ (569.76)
106) 1-0-Eicosanyl-sn-glycero-3-phospho-N,N-dimethyl-N-(diHP)-ethylammonium (n = 2)
$C_{30}H_{64}NO_8P$ (597.81)
107) 1-0-Behenyl-sn-glycero-3-phospho-N,N-dimethyl-N-(diHP)-ethylammonium (n = 2)
$C_{32}H_{68}NO_8P$ (625.86)
108) 1-Palmitoyl-sn-glycero-3-phospho-N,N-dimethyl-N-(diHP)-propylammonium (n = 3)
$C_{27}H_{56}NO_9P$ (569.71)
109) 1-Stearoyl-sn-glycero-3-phospho-N,N-dimethyl-N-(diHP)-propylammonium (n = 3)
$C_{29}H_{60}NO_9P$ (597.77)
110) 1-Behenoyl-sn-glycero-3-phospho-N,N-dimethyl-N-(diHP)-propylammonium (n = 3)
$C_{33}H_{68}NO_9P$ (653.87)
111) 1-Erucoyl-sn-glycero-3-phospho-N,N-dimethyl-N-(diHP)-propylammonium (n = 3)
$C_{33}H_{66}NO_9P$ (651.86)
112) 1-Nervonoyl-sn-glycero-3-phospho-N,N-dimethyl-N-(diHP)-propylammonium (n = 3)
$C_{35}H_{70}NO_9P$ (679.91)
113) 1-Stearoyl-sn-glycero-3-phospho-N,N-dimethyl-N-(diHP)-butylammonium (n = 4)
$C_{30}H_{62}NO_9P$ (611.79)
114) 1-Erucoyl-sn-glycero-3-phospho-N,N-dimethyl-N-(diHP)-butylammonium (n = 4)
$C_{34}H_{68}NO_9P$ (665.88)
115) 1-Stearoyl-sn-glycero-3-phospho-N,N-dimethyl-N-(diHP)-hexylammonium (n = 6)
$C_{32}H_{66}NO_9P$ (639.85)
116) 1-Erucoyl-sn-glycero-3-phospho-N,N-dimethyl-N-(diHP)-hexylammonium (n = 6)
$C_{36}H_{72}NO_8P$ (693.94)

Examples of single-chain glycerophospho-N,N-dimethyl-N-(2-hydroxypropyl-3,1-O,O-dihydroxypropyl)alkylammonium compounds (A=0; n=2–6; $R_3$, $CH_3$; m=1; x=0; y=1; z=2)

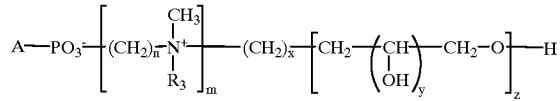

Formula I

| | | |
|---|---|---|
| 117) | 1-Stearoyl-sn-glycero-3-phospho-N,N-dimethyl-N-($HP_1$-$diHP_2$)-ethylammonium (n = 2) $C_{31}H_{64}NO_{11}P$ | (657.82) |
| 118) | 1-Arachinoyl-sn-glycero-3-phospho-N,N-dimethyl-N-($HP_1$-$diHP_2$)-ethylammonium (n = 2) $C_{33}H_{68}NO_{11}P$ | (685.87) |
| 119) | 1-Erucoyl-sn-glycero-3-phospho-N,N-dimethyl-N-($HP_1$-$diHP_2$)-ethylammonium (n = 2) $C_{35}H_{70}NO_{11}P$ | (711.91) |
| 120) | 1-Nervonoyl-sn-glycero-3-phospho-N,N-dimethyl-N-($HP_1$-$diHP_2$)-ethylammonium (n = 2) $C_{37}H_{74}NO_{11}P$ | (739.96) |
| 121) | 1-0-Octadecyl-sn-glycero-3-phospho-N,N-dimethyl-N-($HP_1$-$diHP_2$)-ethylammonium (n = 2) $C_{31}H_{66}NO_{10}P$ | (643.83) |
| 122) | 1-0-Behenyl-sn-glycero-3-phospho-N,N-dimethyl-N-($HP_1$-$diHP_2$)-ethylammonium (n = 2) $C_{35}H_{74}NO_{10}P$ | (699.94) |
| 123) | 1-Stearoyl-sn-glycero-3-phospho-N,N-dimethyl-N-($HP_1$-$diHP_2$)-propylammonium (n = 3) $C_{32}H_{66}NO_{11}P$ | (671.84) |
| 124) | 1-Erucoyl-sn-glycero-3-phospho-N,N-dimethyl-N-($HP_1$-$diHP_2$)-propylammonium (n = 3) $C_{36}H_{72}NO_{11}P$ | (725.94) |
| 125) | 1-Erucoyl-sn-glycero-3-phospho-N,N-dimethyl-N-($HP_1$-$diHP_2$)-butylammonium (n = 4) $C_{37}H_{74}NO_{11}P$ | (739.98) |
| 126) | 1-Erucoyl-sn-glycero-3-phospho-N,N-dimethyl-N-($HP_1$-$diHP_2$)-hexylammonium (n = 6) $C_{39}H_{78}NO_{11}P$ | (768.04) |
| 127) | 1-Nervonoyl-sn-glycero-3-phospho-N,N-dimethyl-N-($HP_1$-$diHP_2$)-propylammonium (n = 3) $C_{38}H_{76}NO_{11}P$ | (754.01) |
| 128) | 1-Nervonoyl-sn-glycero-3-phospho-N,N-dimethyl-N-($HP_1$-$diHP_2$)-butylammonium (n = 4) $C_{39}H_{78}NO_{11}P$ | (768.04) |

Examples of single-chain glycerophospho-N,N-dimethyl-N-(2-hydroxypropyl-3,1-O,O-2-hydroxypropyl-3,1-O,O-dihydroxypropyl)alkylammonium compounds (A=a; n 2–6; $R_3$, $CH_3$; n=1; x=0; y=1; z=3)

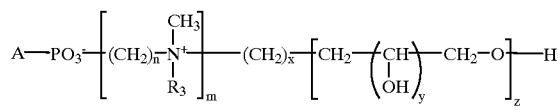

Formula I

| | | |
|---|---|---|
| 129) | 1-Stearoyl-sn-glycero-3-phospho-N,N-dimethyl-N-($HP_1$-$HP_2$-$diHP_3$)-ethylammonium (n = 2) $C_{34}H_{70}NO_{13}P$ | (731.90) |
| 130) | 1-Erucoyl-sn-glycero-3-phospho-N,N-dimethyl-N-($HP_1$-$HP_2$-$diHP_3$)-ethylammonium (n = 2) $C_{38}H_{76}NO_{13}P$ | (785.99) |
| 131) | 1-Nervonoyl-sn-glycero-3-phospho-N,N-dimethyl-N-($HP_1$-$HP_2$-$diHP_3$)-ethylammonium (n = 2) $C_{40}H_{80}NO_{13}P$ | (814.04) |
| 132) | 1-Erucoyl-sn-glycero-3-phospho-N,N-dimethyl-N-($HP_1$-$HP_2$-$diHP_3$)-propylammonium (n = 3) $C_{39}H_{78}NO_{13}P$ | (800.01) |
| 133) | 1-Nervonoyl-sn-glycero-3-phospho-N,N-dimethyl-N-($HP_1$-$HP_2$-$diHP_3$)-propylammonium (n = 3) $C_{41}H_{82}NO_{13}P$ | (828.07) |
| 134) | 1-Erucoyl-sn-glycero-3-phospho-N,N-dimethyl-N-($HP_1$-$HP_2$-$diHP_3$)-butylammonium (n = 4) $C_{40}H_{80}NO_{13}P$ | (814.04) |
| 135) | 1-Erucoyl-sn-glycero-3-phospho-N,N-dimethyl-N-($HP_1$-$HP_2$-$diHP_3$)-hexylammonium (n = 6) $C_{42}H_{84}NO_{13}P$ | (842.09) |

Examples of single-chain glycerophospho compounds not hydroxylated on the nitrogen (A=a; n=3; $R_3$, $CH_3$; m=1 x=1; z=0)

Formula I $$A-PO_3^{-}-\left[(CH_2)_{\overline{n}}-\underset{R_3}{\overset{CH_3}{\underset{|}{N^+}}}-\right]_m(CH_2)_{\overline{x}}\left[CH_2-\left(\underset{OH}{\overset{|}{CH}}\right)_y-CH_2-O\right]_z-H$$

| | | |
|---|---|---|
| 136) | 1-Palmitoyl-sn-glycero-3-phospho-N,N,N-trimethyl-propylammonium (n = 3) $C_{25}H_{52}NO_7P$ | (509.66) |
| 137) | 1-Stearoyl-sn-glycero-3-phospho-N,N,N-trimethyl-propylammonium (n = 3) $C_{27}H_{56}NO_7P$ | (537.71) |
| 138) | 1-Behenoyl-sn-glycero-3-phospho-N,N,N-trimethyl-propylammonium (n = 3) $C_{31}H_{64}NO_2P$ | (593.82) |
| 139) | 1-Erucoyl-sn-glycero-3-phospho-N,N,N-trimethyl-propylammonium (n = 3) $C_{31}H_{62}NO_7P$ | (591.81) |
| 140) | 1-Nervonoyl-sn-glycero-3-phospho-N,N,N-trimethyl-propylammonium (n = 3) $C_{33}H_{66}NO_7P$ | (619.86) |

Examples of ω, ω'-alkanediol-phospho-N,N-dimethyl-N-dihydroxypropylalkylammonium compounds A=b; n=2–4; $R_3$, $CH_3$; m=1; x=0; y=1; z=1)

Formula I $$A-PO_3^{-}-\left[(CH_2)_{\overline{n}}-\underset{R_3}{\overset{CH_3}{\underset{|}{N^+}}}-\right]_m(CH_2)_{\overline{x}}\left[CH_2-\left(\underset{OH}{\overset{|}{CH}}\right)_y-CH_2-O\right]_z-H$$

| | | |
|---|---|---|
| 141) | 1-Stearoyl-ethylene glycol-phospho-N,N-dimethyl-N-dihydroxypropylethylammonium (n = 2) $C_{27}H_{56}NO_8P$ | (553.71) |

Formula I $$A-PO_3^- \left[(CH_2)_{\overline{n}} \underset{R_3}{\overset{CH_3}{\underset{|}{\overset{|}{N^+}}}} \right]_m -(CH_2)_{\overline{x}} \left[CH_2-\left(\underset{OH}{\overset{|}{CH}}\right)_y - CH_2 - O \right]_z - H$$

142) 1-Behenoyl-1,3-propanediol-phospho-N,N-dimethyl-
N-dihydroxypropylethylammonium (n = 2)
$C_{32}H_{66}NO_8P$ (623.85)
143) 1-Stearoyl-1,3-propanediol-phospho-N,N-dimethyl-
N-dihydroxypropylethylammonium (n = 2)
$C_{28}H_{58}NO_8P$ (567.74)
144) 1-Erucoyl-1,3-propanediol-phospho-N,N-dimethyl-
N-dihydroxypropylethylammonium (n = 2)
$C_{32}H_{64}NO_8P$ (621.83)
145) 1-Erucoyl-1,3-propanediol-phospho-N,N-dimethyl-
N-dihydroxypropylpropylammonium (n = 3)
$C_{33}H_{66}NO_8P$ (635.86)
146) 1-Erucoyl-1,3-propanediol-phospho-N,N-dimethyl-
N-dihydroxypropylbutylammonium (n = 4)
$C_{34}H_{68}NO_8P$ (649.88)

Examples of 1,2-alkanediol-phospho-N,N-dimethyl-
N-dihydroxypropylalkylammonium compounds (A=b; n=2–4; $R_3$, $CH_3$; m=1; x=0; y=1; z=1)

Formula I $$A-PO_3^- \left[(CH_2)_{\overline{n}} \underset{R_3}{\overset{CH_3}{\underset{|}{\overset{|}{N^+}}}} \right]_m -(CH_2)_{\overline{x}} \left[CH_2-\left(\underset{OH}{\overset{|}{CH}}\right)_y - CH_2 - O \right]_z - H$$

147) 2-Erucoyl-1,2-propanediol-phospho-N,N-dimethyl-
N-dihydroxypropylethylammonium
$C_{32}H_{64}NO_8P$ (621.33)
148) 1-Erucoyl-1,2-propanediol-phospho-N,N-dimethyl-
N-dihydroxypropylethylammonium
$C_{32}H_{64}NO_8P$ (621.33)
149) 2-Erucoyl-1,2-propanediol-phospho-N,N-dimethyl-
N-dihydroxypropylpropylammonium
$C_{33}H_{66}NO_8P$ (635.86)
150) 1-Erucoyl-1,2-propanediol-phospho-N,N-dimethyl-
N-dihydroxypropylbutylammonium
$C_{34}H_{68}NO_8P$ (649.88)

Examples of ω,ω'-alkanediol-phospho-N,N-
dimethyl-N-(2-hydroxypropyl)-3,1-O,O-
dihydroxypropyl)alkylammonium compounds (A=b; n=2–4; $R_3$, $CH_3$; m=1, x=0; y=1; z=2)

Formula I $$A-PO_3^- \left[(CH_2)_{\overline{n}} \underset{R_3}{\overset{CH_3}{\underset{|}{\overset{|}{N^+}}}} \right]_m -(CH_2)_{\overline{x}} \left[CH_2-\left(\underset{OH}{\overset{|}{CH}}\right)_y - CH_2 - O \right]_z - H$$

151) 1-Stearoyl-ethylene glycol-phospho-N,N-dimethyl-
N-(2-hydroxypropyl)-3,1-O,O-dihydroxypropyl)ethylammonium
$C_{30}H_{62}NO_{10}P$ (627.79)

Formula I $$A-PO_3^- \left[(CH_2)_{\overline{n}} \underset{R_3}{\overset{CH_3}{\underset{|}{\overset{|}{N^+}}}} \right]_m -(CH_2)_{\overline{x}} \left[CH_2-\left(\underset{OH}{\overset{|}{CH}}\right)_y - CH_2 - O \right]_z - H$$

152) 1-Behenoyl-1,3-propanediol-phospho-N,N-dimethyl-
N-(2-hydroxypropyl-3,1-O,O-dihydroxypropyl)ethylammonium
$C_{35}H_{72}NO_{10}P$ (697.93)
153) 1-Stearoyl-1,3-propanediol-phospho-N,N-dimethyl-
N-(2-hydroxypropyl)-3,1-O,O-dihydroxypropylethylammonium
$C_{31}H_{64}NO_{10}P$ (641.82)
154) 1-Erucoyl-1,3-propanediol-phospho-N,N-dimethyl-
N-(2-hydroxypropyl-3,1-O,O-dihydroxypropyl)ethylammonium
$C_{35}H_{70}NO_{10}P$ (695.91)
155) 1-Erucoyl-1,3-propanediol-phospho-N,N-dimethyl-
N-(2-hydroxypropyl-3,1-O,O-dihydroxypropyl)propylammonium
$C_{36}H_{72}NO_{10}P$ (709.94)
156) 1-Erucoyl-1,3-propanediol-phospho-N,N-dimethyl-
N-(2-hydroxypropyl-3,1-O,O-dihydroxypropyl)butylammonium
$C_{37}H_{74}NO_{10}P$ (723.96)
157) 1-Erucoyl-1,4-butanediol-phospho-N,N-dimethyl-
N-(2-hydroxypropyl-3,1-O,O-dihydroxypropyl)propylammonium
$C_{37}H_{74}NO_{10}P$ (723.96)
158) 1-Erucoyl-1,6-hexanediol-phospho-N,N-dimethyl-
N-(2-hydroxypropyl-3,1-O,O-dihydroxypropyl)propylammonium
$C_{39}H_{78}NO_{10}P$ (752.02)
159) 1-Erucoyl-1,8-octanediol-phospho-N,N-dimethyl-
N-(2-hydroxypropyl)-3,1-O,O-dihydroxypropyl)propylammonium
$C_{41}H_{82}NO_{10}P$ (780.07)

Examples of 1,2-alkanediol-phospho-N,N-dimethyl-
N-(2-hydroxypropyl-3,1-O,O-dihydroxypropyl)
alkylammonium compounds (A=b; n=2–4; $R_3$, $CH_3$; m=1; x=0; y=1; z=2)

Formula I $$A-PO_3^- \left[(CH_2)_{\overline{n}} \underset{R_3}{\overset{CH_3}{\underset{|}{\overset{|}{N^+}}}} \right]_m -(CH_2)_{\overline{x}} \left[CH_2-\left(\underset{OH}{\overset{|}{CH}}\right)_y - CH_2 - O \right]_z - H$$

160) 2-Erucoyl-1,2-propanediol-phospho-N,N-dimethyl-
N-(2-hydroxypropyl-3,1-O,O-dihydroxypropyl)ethylammonium
$C_{35}H_{70}NO_{10}P$ (695.91)
161) 1-Erucoyl-1,2-propanediol-phospho-N,N-dimethyl-
N-(2-hydroxypropyl-3,1-O,O-dihydroxypropyl)ethylammonium
$C_{35}H_{70}NO_{10}P$ (695.91)
162) 2-Erucoyl-1,2-propanediol-phospho-N,N-dimethyl-
N-(2-hydroxypropyl-3,1-O,O-dihydroxypropyl)propylammonium
$C_{36}H_{72}NO_{10}P$ (709.94)
163) 1-Erucoyl-1,2-propanediol-phospho-N,N-dimethyl-
N-(2-hydroxypropyl-3,1-O,O-dihydroxypropyl)butylammonium
$C_{37}H_{74}NO_{10}P$ (723.96)
164) 1-Erucoyl-1,2-butanediol-phospho-N,N-dimethyl-
N-(2-hydroxypropyl-3,1-O,O-dihydroxypropyl)propylammonium
$C_{37}H_{74}NO_{10}P$ (723.96)
165) 1-Erucoyl-1,2-hexanediol-phospho-N,N-dimethyl-
N-(2-hydroxypropyl-3,1-O,O-dihydroxypropyl)propylammonium
$C_{39}H_{78}NO_{10}P$ (752.02)
166) 1-Erucoyl-1,2-octanediol-phospho-N,N-dimethyl-
N-(2-hydroxypropyl-3,1-O,O-dihydroxypropyl)propylammonium
$C_{41}H_{82}NO_{10}P$ (780.07)

Examples of ω,ω'-alkanediol-N,N-dimethyl-N-(2-
hydroxypropyl-3,1-O,O-2-hydroxypropyl-3,1-O,O-
dihydroxypropyl)alkylammonium compounds
Abbreviation:
HP=2-Hydroxypropyl diHP=Dihydroxypropyl
(A=b ; n=2–6; R, $CH_3$; m=1; x=0; y=1; z=3)

Formula I $$A-PO_3^- - \left[(CH_2)_{\overline{n}} - \underset{R_3}{\overset{\overset{\displaystyle CH_3}{|}}{N^+}} - \right]_m (CH_2)_{\overline{x}} - \left[CH_2 - \left(\underset{OH}{\overset{|}{CH}}\right)_y - CH_2-O\right]_z - H$$

| | | |
|---|---|---|
| 167) | 1-Oleoyl-ethylene glycol-phospho-N,N-dimethyl-N-($HP_1$-$HP_2$-$diHP_3$)-ethylammonium | |
| | $C_{34}H_{68}NO_{12}P$ | (713.88) |
| 168) | 1-Erucoyl-1,3-propanediol-phospho-N,N-dimethyl N-($HP_1$-$HP_2$-$diHP_3$)-ethylammonium | |
| | $C_{38}H_{76}NO_{12}P$ | (769.99) |
| 169) | 1-Oleoyl-1,3-propanediol-phospho-N,N-dimethyl-N-($HP_1$-$HP_2$-$diHP_3$)-propylammonium | |
| | $C_{35}H_{70}NO_{12}P$ | (727.91) |
| 170) | 1-Erucoyl-1,3-propanediol-phospho-N,N-dimethyl N-($HP_1$-$HP_2$-$diHP_3$)-propylammonium | |
| | $C_{39}H_{78}NO_{12}P$ | (784.01) |
| 171) | 1-Erucoyl-1,3-propanediol-phospho-N,N-dimethyl-N-($HP_1$-$HP_2$-$diHP_3$)-butylammonium | |
| | $C_{40}H_{80}NO_{12}P$ | (798.04) |
| 172) | 1-Erucoyl-1,3-propanediol-phospho-N,N-dimethyl-N-($HP_1$-$HP_2$-$diHP_3$)-hexylammonium | |
| | $C_{42}H_{84}NO_{12}P$ | (826.10) |

Examples of alkanediol-phospho compounds not hydroxylated on the nitrogen (A=b; n=2–6; R, $CH_3$; m=1; x=1; z=0)

Formula I $$A-PO_3^- - \left[(CH_2)_{\overline{n}} - \underset{R_3}{\overset{\overset{\displaystyle CH_3}{|}}{N^+}} - \right]_m (CH_2)_{\overline{x}} - \left[CH_2 - \left(\underset{OH}{\overset{|}{CH}}\right)_y - CH_2-O\right]_z - H$$

| | | |
|---|---|---|
| 173) | 1-Erucoyl-ethylene glycol-phospho-N,N,N-trimethylpropylammonium | |
| | $C_{30}H_{60}NO_6P$ | (561.78) |
| 174) | 1-Arachinoyl-1,3-propanediol-phospho-N,N,N-trimethylpropylammonium | |
| | $C_{29}H_{69}NO_6P$ | (549.77) |
| 175) | 1-Stearoyl-1,3-propanediol-phospho-N,N,N-trimethylpropylammonium | |
| | $C_{27}H_{56}NO_6P$ | (521.71) |
| 176) | 1-Erucoyl-1,3-propanediol-phospho-N,N,N-trimethyl-propylammonium | |
| | $C_{31}H_{62}NO_6P$ | (575.81) |
| 177) | 1-Erucoyl-1,3-propanediol-phospho-N,N,N-trimethyl-butylammonium | |
| | $C_{32}H_{64}NO_6P$ | (589.83) |
| 178) | 1-Erucoyl-1,3-propanediol-phospho-N,N,N-trimethyl-pentylammonium | |
| | $C_{33}H_{66}NO_6$ | (603.86) |
| 179) | 1-Erucoyl-1,2-propanediol-phospho-N,N,N-trimethyl-propylammonium | |
| | $C_{31}H_{62}NO_6P$ | (575.81) |
| 180) | 2-Erucoyl-1,2-propanediol-phospho-N,N,N-trimethyl-propylammonium | |
| | $C_{31}H_{62}NO_6P$ | (575.81) |
| 181) | 1-Erucoyl-1,2-propanediol-phospho-N,N,N-trimethyl-butylammonium | |
| | $C_{32}H_{64}NO_6P$ | (589.83) |
| 182) | 1-Erucoyl-1,2-propanediol-phospho-N,N,N-trimethyl-hexylammonium | |
| | $C_{34}H_{68}NO_6P$ | (617.92) |

3) Active Ingredients

It was found in earlier investigations that alkylphosphocholines have antitumour activity only when the phosphateammonium distance is two C atoms, that is to say corresponds to phosphocholine (n=2 in the general formula I). Compounds with a distance of n>2 had no activity. The active ingredients were administered orally in these earlier investigations.

We have now found, surprisingly, that erucylphospho compounds with phosphateammonium distances of >2 have excellent antitumour activity which is in fact superior to that of alkylphosphocholines when these substances are administered intravenously, as the following comparison shows:

Erucylphosphocholine (n=2 in general formula I)

The substance forms gel-like structures in water and therefore can be administered intravenously only with difficulty in relatively high concentrations. Erucylphosphocholine has only a slight long-term effect in the animal model of methylnitrosourea-induced mammary carcinoma. Tumour growth is observed again only 7 days after discontinuation of the therapy.

Erucylphospho-N,N,N-trimethylpropylammonium (n=3)

The substance is readily soluble in water, forms no gels and can be administered intravenously without difficulty. It can therefore also be used as solubilizer. However, its long-term effect in the above animal model is particularly noteworthy and impressive. No new tumour growth is observed even 4 weeks after discontinuation of the therapy.

Examples of alkylphospho-N,N,N-dimethyl-N-dihydroxypropylalkylammonium compounds (A=c; n=2–6; $R_3$, $CH_3$; m=1; x=0;y=1;z=1)

Formula I $$A-PO_3^- - \left[(CH_2)_{\overline{n}} - \underset{R_3}{\overset{\overset{\displaystyle CH_3}{|}}{N^+}} - \right]_m (CH_2)_{\overline{x}} - \left[CH_2 - \left(\underset{OH}{\overset{|}{CH}}\right)_y - CH_2-O\right]_z - H$$

| | | |
|---|---|---|
| 183) | Hexadecylphospho-N,N-dimethyl-N-dihydroxypropyl-ethylammonium | |
| | $C_{23}H_{50}NO_6P$ | (467.62) |
| 184) | Octadecylphospho-N,N-dimethyl-N-dihydroxypropyl-ethylammonium | |
| | $C_{25}H_{54}NO_6P$ | (495.68) |
| 185) | Erucylphospho-N,N-dimethyl-N-dihydroxypropyl-ethylammonium | |
| | $C_{29}H_{60}NO_6P$ | (549.77) |
| 186) | Erucylphospho-N,N-dimethyl-N-dihydroxypropyl-propylammonium | |
| | $C_{30}H_{62}NO_6P$ | (563.80) |
| 187) | Erucylphospho-N,N-dimethyl-N-dihydroxypropyl-butylammonium | |
| | $C_{31}H_{64}NO_6P$ | (577.82) |
| 188) | Erucylphospho-N,N-dimethyl-N-dihydroxypropyl-hexylammonium | |
| | $C_{32}H_{68}NO_6P$ | (605.88) |
| 189) | Oleylphospho-N,N-dimethyl-N-dihydroxypropyl-ethylammonium | |
| | $C_{25}H_{52}NO_6P$ | (493.66) |
| 190) | Oleylphospho-N,N-dimethyl-N-dihydroxypropyl-propylammonium | |
| | $C_{26}H_{54}NO_6P$ | (507.69) |

-continued

Formula I $$A-PO_3^- \left[ (CH_2)_n-\underset{R_3}{\overset{CH_3}{\underset{|}{N^+}}}-\right]_m (CH_2)_x \left[ CH_2-\left(\underset{OH}{\overset{}{CH}}\right)_y-CH_2-O \right]_z H$$

| | | |
|---|---|---|
| 191) | Oleylphospho-N,N-dimethyl-N-dihydroxypropyl-butylammonium | |
| | $C_{27}H_{56}NO_6P$ | (521.21) |
| 192) | (Z-11)-Eicosenylphospho-N,N-dimethyl-N-dihydroxy-propyl-ethylammonium | |
| | $C_{27}H_{56}NO_6P$ | (521.21) |
| 193) | (Z-11)-Eicosenylphospho-N,N-dimethyl-N-dihydroxy-propyl-propylammonium | |
| | $C_{28}H_{58}NO_6P$ | (535.74) |
| 194) | (Z-11)-Eicosenylphospho-N,N-dimethyl-N-dihydroxy-propyl-butylammonium | |
| | $C_{29}H_{60}NO_6P$ | (549.77) |
| 195) | (Z-11)-Eicosenylphospho-N,N-dimethyl-N-dihydroxy-propyl-pentylammonium | |
| | $C_{30}H_{62}NO_6P$ | (563.80) |
| 196) | (Z-11)-Eicosenylphospho-N,N-dimethyl-N-dihydroxy-propyl-hexylammonium | |
| | $C_{31}H_{64}NO_6P$ | (577.82) |

Examples of alkylphospho-N,N-dimethyl-N-(2-hydroxypropyl-1,2-dihydroxypropyl)alkylammonium 1: (A=C; n=2–6; $R_3$, $CH_3$; m=1; x=0; y=1; z=2)

Formula I $$A-PO_3^- \left[ (CH_2)_n-\underset{R_3}{\overset{CH_3}{\underset{|}{N^+}}}-\right]_m (CH_2)_x \left[ CH_2-\left(\underset{OH}{\overset{}{CH}}\right)_y-CH_2-O \right]_z H$$

| | | |
|---|---|---|
| 197) | Hexadecyl-phospho-N,N-dimethyl-N-(HP$_1$-diHP$_2$)-ethyl-ammonium | |
| | $C_{26}H_{56}NO_8P$ | (541.70) |
| 198) | Octadecyl-phospho-N,N-dimethyl-N-(HP$_1$-diHP$_2$)-ethyl-ammonium | |
| | $C_{28}H_{60}NO_8P$ | (569.76) |
| 199) | Erucyl-phospho-N,N-dimethyl-N-(HP$_1$-diHP$_2$)-ethyl-ammonium | |
| | $C_{32}H_{66}NO_8P$ | (623.85) |
| 200) | Erucyl-phospho-N,N-dimethyl-N-(HP$_1$-diHP$_2$)-propyl-ammonium | |
| | $C_{33}H_{68}NO_8P$ | (637.87) |
| 201) | Erucyl-phospho-N,N-dimethyl-N-(HP$_1$-diHP$_2$)-butyl-ammonium | |
| | $C_{34}H_{70}NO_8P$ | (651.90) |
| 202) | Erucyl-phospho-N,N-dimethyl-N-(HP$_1$-diHP$_2$)-hexyl-ammonium | |
| | $C_{36}H_{74}NO_8P$ | (679.95) |
| 203) | Oleyl-phospho-N,N-dimethyl-N-(HP$_1$-diHP$_2$)-ethyl-ammonium | |
| | $C_{28}H_{58}NO_8P$ | (567.74) |
| 204) | Oleyl-phospho-N,N-dimethyl-N-(HP$_1$-diHP$_2$)-propyl-ammonium | |
| | $C_{29}H_{60}NO_8P$ | (581.77) |
| 205) | Oleyl-phospho-N,N-dimethyl-N-(HP$_1$-diHP$_2$)-butyl-ammonium | |
| | $C_{30}H_{62}NO_8P$ | (595.79) |
| 206) | (Z-11)-Eicosenyl-phospho-N,N-dimethyl-N-(HP$_1$-diHP$_2$)-ethylammonium | |
| | $C_{30}H_{62}NO_8P$ | (595.79) |
| 207) | (Z-11)-Eicosenyl-phospho-N,N-dimethyl-N-(HP$_1$-diHP$_2$)-propylammonium | |
| | $C_{30}H_{64}NO_6P$ | (609.82) |
| 208) | (Z-11)-Eicosenyl-phospho-N,N-dimethyl-N-(HP$_1$-diHP$_2$)-butylammonium | |
| | $C_{32}H_{66}NO_8P$ | (623.85) |

Examples of alkylphospho-N,N-dimethyl-N-(2-hydroxypropyl-3,1-O,O-hydroxypropyl-3,1-O,O-1,2-dihydroxypropyl)alkylammonium compounds (A=c; n=2–4; $R_3$, $CH_3$; m=1; x=0; y=1; z=3)

Formula I $$A-PO_3^- \left[ (CH_2)_n-\underset{R_3}{\overset{CH_3}{\underset{|}{N^+}}}-\right]_m (CH_2)_x \left[ CH_2-\left(\underset{OH}{\overset{}{CH}}\right)_y-CH_2-O \right]_z H$$

| | | |
|---|---|---|
| 209) | Hexadecyl-phospho-N,N-dimethyl-N-(HP$_1$-HP$_2$-diHP$_3$)-ethylammonium | |
| | $C_{29}H_{62}NO_{10}P$ | (615.78) |
| 210) | Octadecyl-phospho-N,N-dimethyl-N-(HP$_1$-HP$_2$-diHP$_3$)-ethylammonium | |
| | $C_{31}H_{66}NO_{10}P$ | (643.83) |
| 211) | Oleol-phospho-N,N-dimethyl-N-(HP$_1$-HP$_2$-diHP$_3$)-ethyl-ammonium | |
| | $C_{31}H_{64}NO_{10}P$ | (641.82) |
| 212) | (Z-11)-Eicosenyl-phospho-N,N-dimethyl-N-(HP$_1$-HP$_2$-diHP$_3$)-ethylammonium | |
| | $C_{33}H_{68}NO_{10}P$ | (669.87) |
| 213) | (Z-11)-Eicosenyl-phospho-N,N-dimethyl-N-(HP$_1$-HP$_2$-diHP$_3$)-propylammonium | |
| | $C_{34}H_{70}NO_{10}P$ | (683.90) |
| 214) | (Z-11)-Eicosenyl-phospho-N,N-dimethyl-N-(HP$_1$-HP$_2$-diHP$_3$)-butylammonium | |
| | $C_{35}H_{72}NO_{10}P$ | (697.93) |
| 215) | Erucyl-phospho-N,N-dimethyl-N-(HP$_1$-HP$_2$-diHP$_3$)-ethylammonium | |
| | $C_{35}H_{72}NO_{10}P$ | (697.93) |
| 216) | Erucyl-phospho-N,N-dimethyl-N-(HP$_1$-HP$_2$-diHP$_3$)-propylammonium | |
| | $C_{36}H_{74}NO_{10}P$ | (711.95) |

Examples of alkylphospho compounds having no dihydroxy-alkyl radicals on the nitrogen (A=a; n=3–6; $R_3$, $CH_3$; m=1, , x=1–3; z=0)

Formula I $$A-PO_3^- \left[ (CH_2)_n-\underset{R_3}{\overset{CH_3}{\underset{|}{N^+}}}-\right]_m (CH_2)_x \left[ CH_2-\left(\underset{OH}{\overset{}{CH}}\right)_y-CH_2-O \right]_z H$$

| | | |
|---|---|---|
| 217) | Erucyl-phospho-N,N,N-trimethyl-propylammonium | |
| | $C_{28}H_{58}NO_4P$ | (503.74) |

-continued

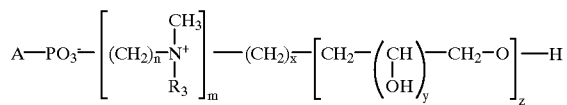

218) Erucyl-phospho-N,N-dimethyl-N-ethyl-propylammonium
 $C_{29}H_{60}NO_4P$ (517.77)
219) Erucyl-phospho-N,N-dimethyl-N-propyl-propyl-ammonium
 $C_{30}H_{62}NO_4P$ (531.80)
220) Erucyl-phospho-N,N-dimethyl-N-allyl-propylammonium
 $C_{30}H_{60}NO_4P$ (529.78)
 Rf values of substances 217–240 in the system described:
 Rf 0.30–0.40
221) (Z)-10-Docosenyl-2-phospho-N,N,N-trimethyl-propylammonium
 $C_{28}H_{58}NO_4P$ (503.74)
222) (Z)-10-Docosenyl-2-phospho-N,N-dimethyl-N-ethyl-propylammonium
 $C_{29}H_{60}NO_4P$ (517.77)
223) Erucyl-phospho-N,N,N-trimethyl-butylammonium
 $C_{29}H_{60}NO_4P$ (517.77)
224) Erucyl-phospho-N,N-dimethyl-N-ethyl-butylammonium
 $C_{30}H_{62}NO_4P$ (531.80)
225) Erucyl-phospho-N,N-dimethyl-N-propyl-butylammonium
 $C_{31}H_{64}NO_4P$ (545.82)
226) (Z)-10-Docosenyl-2-phospho-N,N,N-trimethyl-butylammonium
 $C_{29}H_{60}NO_4P$ (517.77)
227) (Z)-11-Eicosenyl-phospho-N,N,N-trimethyl-propylammonium
 $C_{26}H_{54}NO_4P$ (475.69)
228) (Z)-11-Eicosenyl-phospho-N,N-dimethyl-N-ethyl-propylammonium
 $C_{27}H_{56}NO_4P$ (489.72)
229) (Z)-11-Eicosenyl-phospho-N,N-diethyl-N-methyl-propylammonium
 $C_{28}H_{58}NO_4P$ (503.74)
230) (Z)-11-Eicosenyl-phospho-N,N-dimethyl-N-propyl-propylammonium
 $C_{28}H_{58}NO_4P$ (503.74)
231) (Z)-11-Eicosenyl-phospho-N,N,N-trimethyl-butylammonium
 $C_{27}H_{56}NO_4P$ (489.72)
232) (Z)-11-Eicosenyl-phospho-N,N-dimethyl-N-ethyl-butylammonium
 $C_{28}H_{58}NO_4P$ (503.74)
233) (Z)-11-Eicosenyl-phospho-N,N-dimethyl-N-propyl-butylammonium
 $C_{29}H_{60}NO_4P$ (517.77)
234) (Z)-11-Eicosenyl-phospho-N,N-dimethyl-N-alkyl-butylammonium
 $C_{29}H_{58}NO_4P$ (575.75)
235) Oleyl-phospho-N,N,N-trimethyl-propylammonium
 $C_{24}H_{50}NO_4P$ (447.64)
236) Oleyl-phospho-N,N-dimethyl-N-ethyl-propylammonium
 $C_{25}H_{52}NO_4P$ (461.66)
237) Oleyl-phospho-N,N-dimethyl-N-propylene-propyl-ammonium
 $C_{26}H_{54}NO_4P$ (475.69)
238) Oleyl-phospho-N,N,N-trimethyl-butylammonium
 $C_{25}H_{52}NO_4P$ (461.66)
239) Oleyl-phospho-N,N-dimethyl-N-ethyl-butylammonium
 $C_{26}H_{54}NO_4P$ (475.69)
240) Oleyl-phospho-N,N-dimethyl-N-propyl-butylammonium
 $C_{27}H_{56}NO_4P$ (489.72)

Active ingredients based on alkylated (ether) lysolecithins and hydroxylated on the nitrogen (A=a; n=2–4; $R_3$, $CH_3$; m=1; x=0; y=1; z=1–2)

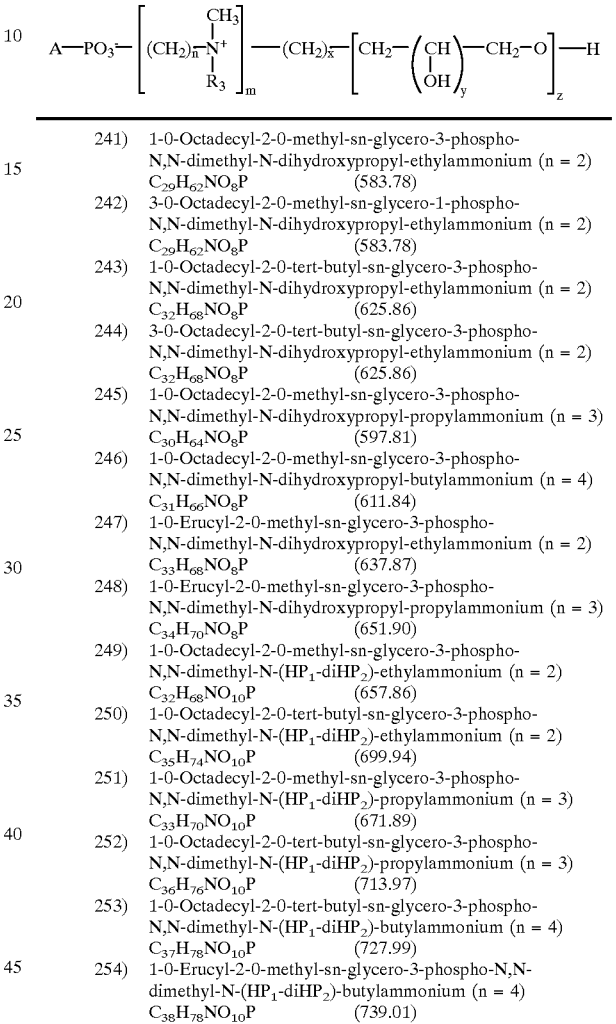

Formula I 241) 1-0-Octadecyl-2-0-methyl-sn-glycero-3-phospho-N,N-dimethyl-N-dihydroxypropyl-ethylammonium (n = 2)
 $C_{29}H_{62}NO_8P$ (583.78)
242) 3-0-Octadecyl-2-0-methyl-sn-glycero-1-phospho-N,N-dimethyl-N-dihydroxypropyl-ethylammonium (n = 2)
 $C_{29}H_{62}NO_8P$ (583.78)
243) 1-0-Octadecyl-2-0-tert-butyl-sn-glycero-3-phospho-N,N-dimethyl-N-dihydroxypropyl-ethylammonium (n = 2)
 $C_{32}H_{68}NO_8P$ (625.86)
244) 3-0-Octadecyl-2-0-tert-butyl-sn-glycero-3-phospho-N,N-dimethyl-N-dihydroxypropyl-ethylammonium (n = 2)
 $C_{32}H_{68}NO_8P$ (625.86)
245) 1-0-Octadecyl-2-0-methyl-sn-glycero-3-phospho-N,N-dimethyl-N-dihydroxypropyl-propylammonium (n = 3)
 $C_{30}H_{64}NO_8P$ (597.81)
246) 1-0-Octadecyl-2-0-methyl-sn-glycero-3-phospho-N,N-dimethyl-N-dihydroxypropyl-butylammonium (n = 4)
 $C_{31}H_{66}NO_8P$ (611.84)
247) 1-0-Erucyl-2-0-methyl-sn-glycero-3-phospho-N,N-dimethyl-N-dihydroxypropyl-ethylammonium (n = 2)
 $C_{33}H_{68}NO_8P$ (637.87)
248) 1-0-Erucyl-2-0-methyl-sn-glycero-3-phospho-N,N-dimethyl-N-dihydroxypropyl-propylammonium (n = 3)
 $C_{34}H_{70}NO_8P$ (651.90)
249) 1-0-Octadecyl-2-0-methyl-sn-glycero-3-phospho-N,N-dimethyl-N-($HP_1$-di$HP_2$)-ethylammonium (n = 2)
 $C_{32}H_{68}NO_{10}P$ (657.86)
250) 1-0-Octadecyl-2-0-tert-butyl-sn-glycero-3-phospho-N,N-dimethyl-N-($HP_1$-di$HP_2$)-ethylammonium (n = 2)
 $C_{35}H_{74}NO_{10}P$ (699.94)
251) 1-0-Octadecyl-2-0-methyl-sn-glycero-3-phospho-N,N-dimethyl-N-($HP_1$-di$HP_2$)-propylammonium (n = 3)
 $C_{33}H_{70}NO_{10}P$ (671.89)
252) 1-0-Octadecyl-2-0-tert-butyl-sn-glycero-3-phospho-N,N-dimethyl-N-($HP_1$-di$HP_2$)-propylammonium (n = 3)
 $C_{36}H_{76}NO_{10}P$ (713.97)
253) 1-0-Octadecyl-2-0-tert-butyl-sn-glycero-3-phospho-N,N-dimethyl-N-($HP_1$-di$HP_2$)-butylammonium (n = 4)
 $C_{37}H_{78}NO_{10}P$ (727.99)
254) 1-0-Erucyl-2-0-methyl-sn-glycero-3-phospho-N,N-dimethyl-N-($HP_1$-di$HP_2$)-butylammonium (n = 4)
 $C_{38}H_{78}NO_{10}P$ (739.01)

Active Ingredients Based on Alkylated (ether) Lysole-cithins and not Hydroxylated on the Nitrogen (A=a; n=3, 4; $R_3$, $CH_3$; m=1; x=1; z=0)

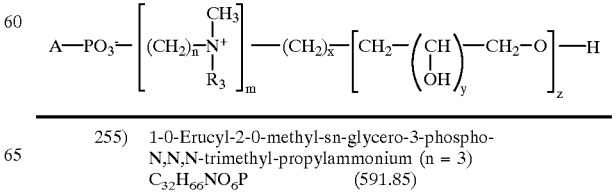

Formula I 255) 1-0-Erucyl-2-0-methyl-sn-glycero-3-phospho-N,N,N-trimethyl-propylammonium (n = 3)
 $C_{32}H_{66}NO_6P$ (591.85)

-continued

Formula I

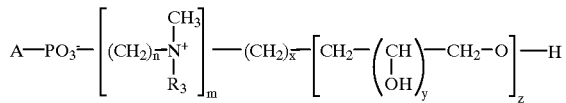

| 256) | 1-O-Erucyl-3-O-methyl-sn-glycero-2-phospho-N,N,N-trimethyl-propylammonium (n = 3) | |
| --- | --- | --- |
| | $C_{32}H_{66}NO_6P$ | (591.85) |
| 257) | 1-O-(Z)-11-Eicosenyl-2-O-methyl-sn-glycero-3-phospho-N,N,N-trimethyl-propylammonium (n = 3) | |
| | $C_{30}H_{62}NO_6P$ | (563.80) |
| 258) | 1-O-(Z)-11-Eicosenyl-2-O-tert-butyl-sn-glycero-3-phospho-N,N,N-trimethyl-propylammonium (n = 3) | |
| | $C_{33}H_{68}NO_6P$ | (605.88) |
| 259) | 1-O-Oleyl-2-O-tert-butyl-sn-glycero-3-phospho-N,N,N-trimethyl-propylammonium (n = 3) | |
| | $C_{31}H_{64}NO_6P$ | (577.82) |
| 260) | 1-O-(Z)-11-Eicosenyl-2-O-tert-butyl-sn-glycero-3-phospho-N,N,N-trimethyl-butylammonium (n = 4) | |
| | $C_{34}H_{70}NO_6P$ | (619.90) |
| 261) | 1-O-Oleyl-2-O-tert-butyl-sn-glycero-3-phospho-N,N,N-trimethyl-butylammonium (n = 4) | |
| | $C_{32}H_{66}NO_6P$ | (591.85) |

Active Ingredients Based on Alkanediol-phospho Compounds and Hydroxylated on the Nitrogen (A=n=2, 3; $R_3$, $CH_3$; m=1; x=0; y=1; z=1)

Formula I

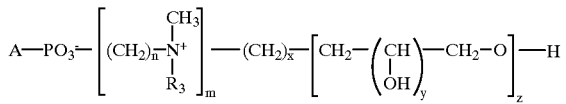

| 262) | 1-O-Erucyl(ethylene glycol)phospho-N,N-dimethyl-N-dihydroxypropylethylammonium | |
| --- | --- | --- |
| | $C_{31}H_{64}NO_7P$ | (593.82) |
| 263) | 1-O-Erucyl-1,3-propanediol-phospho-N,N-dimethyl-N-dihydroxypropylethylammonium | |
| | $C_{32}H_{66}NO_7P$ | (607.85) |
| 264) | 1-O-Erucyl-1,2-propanediol-phospho-N,N-dimethyl-N-dihydroxypropylethylammonium | |
| | $C_{32}H_{66}NO_7P$ | (607.85) |
| 265) | 2-O-Erucyl-1,2-propanediol-phospho-N,N-dimethyl-N-dihydroxypropylethylammonium | |
| | $C_{32}H_{66}NO_7P$ | (607.85) |
| 266) | 1-O-(Z)-11-Eicosenyl-1,2-propanediol-phospho-N,N-dimethyl-N-dihydroxypropylethylammonium | |
| | $C_{30}H_{62}NO_7P$ | (579.49) |
| 267) | 2-O-(Z)-11-Eicosenyl-1,2-propanediol-phospho-N,N-dimethyl-N-dihydroxypropylethylammonium | |
| | $C_{30}H_{62}NO_7P$ | (579.49) |
| 268) | 1-O-Oleyl-1,2-propanediol-phospho-N,N-dimethyl-N-dihydroxypropylethylammonium | |
| | $C_{28}H_{58}NO_7P$ | (551.74) |
| 269) | 2-O-oleyl-1,2-propanediol-phospho-N,N-dimethyl-N-dihydroxypropylethylammonium | |
| | $C_{28}H_{58}NO_7P$ | (551.74) |
| 270) | 2-O-Octadecyl-1,2-propanediol-phospho-N,N-dimethyl-N-dihydroxypropylethylammonium | |
| | $C_{28}H_{60}NO_7P$ | (553.76) |
| 271) | 1-O-Octadecyl-1,2-propanediol-phospho-N,N-dimethyl-N-dihydroxypropylpropylammonium | |
| | $C_{29}H_{62}NO_7P$ | (626.24) |
| 272) | 2-O-Octadecyl-1,2-propanediol-phospho-N,N-dimethyl-N-dihydroxypropylpropylammonium | |
| | $C_{29}H_{62}NO_7P$ | (626.24) |

Active Ingredients Based on Alkanediol-phospho Compounds and not Hydroxylated on the Nitrogen (A=b; n=3; $R_3$, $CH_3$; m=1; x=1; z=0)

Formula I

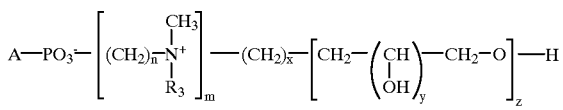

| 273) | 1-O-Erucyl-1,2-propanediol-phospho-N,N,N-tri-methylpropylammonium | |
| --- | --- | --- |
| | $C_{31}H_{64}NO_5P$ | (562.82) |
| 274) | 1-O-Erucyl-1,2-propanediol-phospho-N,N,N-tri-methylpropylammonium | |
| | $C_{31}H_{64}NO_5P$ | (562.82) |
| 275) | 1-O-(Z)-11-Eicosenyl-1,3-propanediol-phospho-N,N,N-trimethylpropylammonium | |
| | $C_{29}H_{60}NO_5P$ | (533.77) |
| 276) | 1-O-Oleyl-1,2-propanediol-phospho-N,N,N-trimethyl-propylammonium | |
| | $C_{27}H_{56}NO_5P$ | (505.72) |
| 277) | 2-O-Oleyl-1,2-propanediol-phospho-N,N,N-trimethyl-propylammonium | |
| | $C_{27}H_{56}NO_5P$ | (505.72) |
| 278) | 1-O-Octadecyl-1,2-propanediol-phospho-N,N,N-propylammonium | |
| | $C_{27}H_{58}NO_5P$ | (507.73) |
| 279) | 2-O-Octadecyl-1,2-propanediol-phospho-N,N,N-trimethylpropylammonium | |
| | $C_{27}H_{58}NO_5P$ | (507.73) |

What is claimed is:

1. A compound of formula

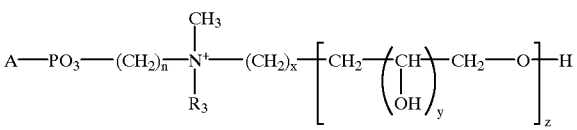

wherein n is an integer from 2 to 8;

$R_3$ is a, b or c, wherein a is 1, 2-dihydroxy propyl, b is a C 1–3 alkyl group when z is >0, and c is a C1–3 alkyl group when n is not 2 and z is 0;

x is an integer from 0 to 8;

y is 1 when z is 1 to 5 or y is 1 to 4 when z is 1;

z is an integer from 0 to 5;

A is selected from the group consisting of a, b and c, wherein a is

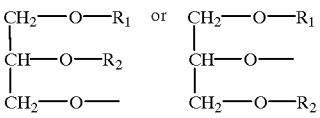

b is

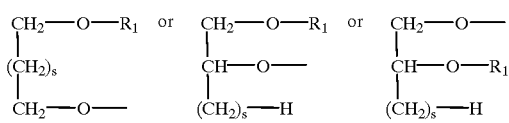

R₁ and R₂ are, independently of each other, a hydrogen atom, a saturated or unsaturated C16–22 acyl or C16–22 alkyl radical, optionally branched or substituted, and s is an integer from 0 to 8; and wherein c is a radical of a primary or secondary alcohol of the formula RO—, where R is a saturated or unsaturated C12–30 alkyl radical with a cis double bond, or a salt thereof.

2. The compound according to claim 1, wherein x is 0, y is 1, and z is 1.

3. The compound according to claim 1, wherein x is 0, y is 1, and z is 2.

4. The compound according to claim 1, wherein x is 0, y is 1, and z is 3.

5. The compound according to claim 1, wherein x is 0, y is 1, and z is 4.

6. The compound according to claim 1, wherein x is 1–3 and z is 0.

7. The compound according to claim 6, wherein x is 1 and z is 0.

8. The compound according to claim 1, wherein n is 2–6.

9. The compound according to claim 8, wherein n is 2–4.

10. The compound according to claim 1, wherein $R_3$ is a $CH_3$ radical.

11. The compound according to claim 1, wherein A is a group of formula a.

12. The compound according to claim 1, wherein A is a group of formula a, and one of $R_1$ and $R_2$ is a hydrogen atom or a C1–3 alkyl chain.

13. The compound according to claim 1, wherein A is a group of formula a, and n is 3–6.

14. The compound according to claim 13, wherein n is 3.

15. The compound according to claim 13, wherein n is 4.

16. The compound according to claim 1, wherein A is a group of formula b.

17. The compound according to claim 1, wherein n is 2.

18. The compound according to claim 1, wherein n is 3.

19. The compound according to claim 1, wherein n is 4.

20. The compound according to claim 1, wherein A is a group of formula c.

21. The compound according to claim 20, wherein n is 3.

22. A liposome comprising a phospholipid, an alkylphospholipid, and a compound of claim 1 at a concentration of 1 to 50% mol of the liposome.

23. A pharmaceutical composition comprising the liposome according to claim 22 having at least one pharmaceutically active agent entrapped within the liposome.

24. The liposome according to claim 22, further comprising cholesterol.

25. A method of delivering a water-insoluble, or a poorly water soluble, active agent to a cell, comprising admixing a compound of claim 1 with the active agent to obtain an admixture, and delivering the admixture to the cell.

26. The method according to claim 25, wherein for the compound of claim 1, $R_1$ is erucic acid.

27. A method of inhibiting a tumor in a subject in need thereof, comprising administering to the subject a tumor-inhibitory effective amount of a compound of claim 1.

28. A method of treating a protozoal disease in a subject in need thereof, comprising administering to the subject a protozoal-inhibitory effective amount of a compound of claim 1.

29. A method of inhibiting a tumor in a subject in need thereof, comprising administering to the subject the liposome of claim 22 having a tumor-inhibitory effective amount of a tumor-inhibitory active agent entrapped within the liposome.

30. A method of treating a protozoal disease in a subject in need thereof, comprising administering to the subject the liposome of claim 22 having a protozoal-inhibitory effective amount of a protozoal-inhibitory active agent entrapped within the liposome.

31. A method of regulating cell proliferation, comprising exposing a cell to the liposome of claim 22 having a cell proliferation regulating amount of a cell proliferation influencing active agent entrapped within the liposome.

* * * * *